(12) United States Patent
Wescott et al.

(10) Patent No.: US 6,984,373 B2
(45) Date of Patent: Jan. 10, 2006

(54) FIBRIN BINDING MOIETIES USEFUL AS IMAGING AGENTS

(75) Inventors: Charles R. Wescott, Belmont, MA (US); James P. Beltzer, Carlisle, MA (US); Aaron K. Sato, Somerville, MA (US)

(73) Assignee: Dyax Corp., Cambridge, MA (US)

( * ) Notice: Subject to any disclaimer, the term of this patent is extended or adjusted under 35 U.S.C. 154(b) by 460 days.

(21) Appl. No.: 10/034,974

(22) Filed: Dec. 21, 2001

(65) Prior Publication Data

US 2003/0143158 A1 Jul. 31, 2003

Related U.S. Application Data

(60) Provisional application No. 60/367,373, filed on Dec. 23, 2000, now abandoned.

(51) Int. Cl.
| | |
|---|---|
| A61B 5/055 | (2006.01) |
| A61B 8/00 | (2006.01) |
| A61B 8/15 | (2006.01) |
| A61K 49/14 | (2006.01) |
| A61K 51/08 | (2006.01) |

(52) U.S. Cl. ............... 424/1.69; 424/9.322; 424/9.411; 424/9.5; 530/326; 530/328

(58) Field of Classification Search ............... 530/326, 530/328; 424/1.69, 9.322, 9.411, 9.5
See application file for complete search history.

(56) References Cited

U.S. PATENT DOCUMENTS

| | | | |
|---|---|---|---|
| 4,808,405 A | 2/1989 | Smith et al. | |
| 5,011,686 A | 4/1991 | Pang | |
| 5,021,556 A | 6/1991 | Srinivasan | |
| 5,075,099 A | 12/1991 | Srinivasan et al. | |
| 5,223,409 A | 6/1993 | Ladner et al. | |
| 5,364,612 A | 11/1994 | Goldenberg | |
| 5,364,613 A | 11/1994 | Sieving et al. | |
| 5,367,080 A | 11/1994 | Toner et al. | |
| 5,632,968 A | 5/1997 | Goldenberg | |
| 5,674,469 A | 10/1997 | Jablonski | |
| 5,720,934 A | 2/1998 | Dean et al. | |
| 5,849,261 A | 12/1998 | Dean et al. | |
| 5,879,658 A | 3/1999 | Dean et al. | |
| 5,886,142 A | 3/1999 | Thakur et al. | |
| 6,001,809 A | 12/1999 | Thorsett et al. | |

FOREIGN PATENT DOCUMENTS

| | | |
|---|---|---|
| EP | 0 297 882 A2 | 1/1989 |
| EP | 0347 078 A1 | 12/1989 |
| WO | WO 91/16353 | 10/1991 |
| WO | WO 93/25241 | 12/1993 |
| WO | WO 95/28967 | 11/1995 |
| WO | WO 96/17628 | 6/1996 |
| WO | WO 96/23524 | 8/1996 |
| WO | WO 97/18841 | 5/1997 |
| WO | WO 97/29783 | 8/1997 |
| WO | WO 98/05364 | 2/1998 |
| WO | WO 98/17324 | 4/1998 |
| WO | WO 98/17796 | 4/1998 |
| WO | WO 98/18495 | 5/1998 |
| WO | WO 98/18496 | 5/1998 |
| WO | WO 98/18497 | 5/1998 |
| WO | WO 98/18498 | 5/1998 |
| WO | WO 98/18501 | 5/1998 |
| WO | WO 98/34631 | 8/1998 |
| WO | WO 98/47538 | 10/1998 |
| WO | WO 98/52618 | 11/1998 |
| WO | WO 98/53857 | 12/1998 |
| WO | WO 98/57666 | 12/1998 |
| WO | WO 01/09188 | 2/2001 |

OTHER PUBLICATIONS

Alavi et al., "Radiolabeled Antifibrin Antibody in the Detection of Venous Thrombosis: Preliminary Results," *Radiology*, 175:79–85 (1990).

Alexander et al., "Intracranial Black–Blood MR Angiography with High–Resolution 3D Fast Spin Echo," *Magnetic Resonance in Medicine*, 40(2):298–310 (1998).

Anderson and Miller, "Fiber Optic Immunochemical Sensor for Continuous, Reversible Measurement of Phenytoin," *Clin. Chem.*, 34(7):1417–1421 (1988).

Bautovich et al., "Detection of Deep Venous Thrombi and Pulmonary Embolus with Technetium–99m–DD–3B6/22 Anti–fibrin Monoclonal Antibody Fab' Fragment," *J. Nucl. Med.*, 35:195–202 (1994).

Edelman et al., "Extracranial Carotid Arteries: Evaluation with "Black–Blood" MR Angiography," *Radiology*, 177(1):45–50 (1990).

Fairbrother et al., "Novel Peptides Selected to Bind Vascular Endothelial Growth Factor Target the Receptor–Binding Site," *Biochemistry*, 37:17754–17764 (1998).

Goodrich et al., "A Quantitative Study of Ramped Radio Frequency, Magnetization Transfer, and Slab Thickness in Three–Dimensional Time–of–Flight Magnetic Resonance Angiography in a Patient Population," *Investigative Radiology*, 31(6):323–332 (1996).

(Continued)

*Primary Examiner*—Robert A. Wax
(74) *Attorney, Agent, or Firm*—Fish & Richardson P.C.

(57) ABSTRACT

The present invention provides binding moieties for fibrin which have a variety of uses wherever detecting, isolating or localizing fibrin, and particularly fibrin as opposed to fibrinogen, is advantageous. Particularly disclosed are synthetic, isolated polypeptides capable of binding fibrin and recognizing the form of polymerized fibrin found in thrombi. In addition, the polypeptides have a slow dissociation rate from fibrin, which improves their ability to form a contrast image at the site of a fibrin clot, making the disclosed binding moieties particularly useful as imaging agents for thrombi.

59 Claims, 4 Drawing Sheets

OTHER PUBLICATIONS

Gronas et al., "Flow–Independent Angiography for Peripheral Vascular Disease: Initial In–Vivo Results," *Journal of Magnetic Resonance Imaging*, 7(4):637–643 (1997).

Harker et al., "Role of Platelets and Thrombosis in Mechanisms of Acute Occlusion and Restenosis After Angioplasty," *Am. J. Cardiology*, 60:20B–28B (1987).

Hermans et al., "Fibrin: Structure and Interactions," *Semin. Thromb. Hemost.*, 8:11–24 (1982).

Hutchinson, "Evanescent Wave Biosensors," *Molec. Biotechnology*, 3:47–54 (1995).

Knight et al., "Fragment $E_1$ Labeled with I–123 in the Detection of Venous Thrombosis," *Radiology*, 156:509–514 (1985).

Lanza et al., "High–Frequency Ultrasonic Detection of Thrombi with a Targeted Contrast System," *Ultrasound in Med. & Bio.*, 23(6):863–870 (1997).

Malmborg et al., "Selection of Binders from Phage Displayed Antibody Libraries Using the BIAcore™ Biosensor," *J. Immunol. Methods*, 198(1):51–57 (1996).

Merrifield, "Solid Phase Peptide Synthesis. I. The Synthesis of a Tetrapeptide," *J. Am. Chem. Soc.*, 85:2149–2154 (1963).

Moskowitz and Budzynski, "The (DD)E Complex is Maintained by a Composite Fibrin Polymerization Site," *Biochemistry*, 33:12937–12944 (1994).

Muto et al., "Initial Clinical Experience with Tc–99m P280, a Synthetic Peptide Useful for Imaging Thrombi and Pulmonary Emboli," *Radiology*, 189(Suppl.), 303 (1993).

Olexa et al., "Structure of Fragment E Species from Human Cross–Linked Fibrin," *Biochemistry*, 20:6139–6145 (1981).

Palabrica et al., "Thrombus Imaging in a Primate Model with Antibodies Specific for an External Membrane Protein of Activated Platelets," *Proc. Natl. Acad. Sci.*, 86:1036–1040 (1989).

Rosebrough et al., "Thrombus Imaging: A Comparison of Radiolabeled GC4 and T2G1s Fibrin–Specific Monoclonal Antibodies," *J. Nuc. Med.*, 31:1048–1054 (1990).

Schuck, "Reliable Determination of Binding Affinity and Kinetics Using Surface Plasmon Resonance Biosensors," *Current Opinion in Biotechnology*, 8:498–502 (1997).

Spraggon et al., "Crystal Structures of Fragment D from Human Fibrinogen and its Crosslinked Counterpart from Fibrin," *Nature*, 389:455–462 (1997).

Thakur et al., "Indium–111 Labeled Platelets: Studies on Preparation and Evaluation of In Vitro and In Vivo Function," *Thromb. Res.*, 9:345–357 (1976).

Peter et al., "Construction and Functional Evaluation of single–Chain Antibody Fusion Protein with Fibrin Targeting and Thrombin Inhibition After Activation by Factor Xa," *Circulation*, 101:1158–1164 (2000).

Achyuthan, K.E. et al., "Factor XIIIa–Derived Peptides Inhibit Transglutaminase Activity", *The Journal of Biological Chemistry*, vol. 268, No. 28, pp. 21284–21292, 1993.

Achyuthan, K.E. et al., "Hierarchies in the Binding of Human Factor XIII, Factor XIIIa, and Endothelial Cell Transglutaminase to Human Plasma Fibrinogen, Fibrin, and Fibronectin", *Molecular and Cellular biochemistry*, vol. 162, pp. 43–49, 1996.

Achyuthan, K.E. et al., "The Binding Sites on Fibrin(ogen) for Guinea Pig Liver Transglutaminase Are Similar to Those of Blood Coagulation Factor XIII", *The Journal of Biological Chemistry*, vol. 163, No. 28, pp. 14296–14301, 1988.

Bevan, M., et al., Accession No. T05787, 1998.

Gray J X et al., "CD97 is a Processed, Seven–Transmembrane, Heterodimeric Receptor Associated with Inflammation," J of Immun, The Williams and Wilkins Co., vol. 157, No. 12, Dec. 15, 1996.

Greenberg, C.S. et al., Isolation of a Fibrin–Binding Fragment from Blood Coagulation Factor XIII Capable of cross–Linking Fibrin(ogen), *Biochem. J.*, vol. 256, pp. 1013–1019, 1988.

Greenberg, C.S. et al., "Transglutaminases: Multifunctional Cross–Linking Enzymes that Stabilise Tissues", *The FASEB Journal*, vol. 5, pp. 3071–3077, 1991.

Greenwald R.B. et al., "PEG Thiazolidine–2–Thione, a Novel Reagent for Facile Protein Modification: Conjugation of Bovine Hemoglobin", *Bioconjugate Chem.*, vol. 7, pp. 638–641, 1996.

Favreau P et al., "Biochemical Characterization and Nuclear Magnetic Resonance Structure of Novel Alpha–Conotoxins Isolated From the Venom of Conus Consors," Biochemistry, American Chemical Society, vol. 38, No. 19, May 11, 1999.

Fischman, A.J. et al., "A Ticket to Ride: Peptide Radiopharmaceuticals", *J. Nucl. Med.*, vol. 34, pp. 2253–2263, 1993.

Hai, T.T et al., Synthesis of Water–Soluble, Nonimmunogenic Polyamide Cross–Linking Agents, *Bioconjugate Chem.*, vol. 9, pp. 645–654, 1998.

Huang, L. et al., "Coupling of Antibodies with Liposomes", *Loposome Technology*, vol. III, pp. 51–62.

Joppich, M. and Luisi, P.L., "Peptides Flanked by Two Polimer Chains, 1", *Makromol. Chem.*, vol. 180, pp. 1381–1384, 1979.

Kim, H.C. et al., The Complete Amino Acid Sequence of the Human Transglutaminase K Enzyme Deduced from the Nucleic Acid Sequences of cDNA Clones, *The Journal of Biological Chemistry*, vol. 266, No. 1, pp. 536–539, 1991.

Kim, S.Y. et al., "The Structure of the Transglutaminase 1 Enzyme", *The Journal of Biological Chemistry*, vol. 269, No. 45, pp. 27979–27986, 1994.

Klibanov, A.L. et al., "Amphipathic Polyethyleneglycols effectively Prolong the Circulation Time of Liposomes", *FEBS*, vol. 268, No. 1, pp. 235–237, 1990.

Lai, T.S. et al., "Carboxyl–Terminal Truncation of Recombinant Factor XIII A–Chains", *The Journal of Biological Chemistry*, vol. 269, No. 40, pp. 24596–24601, 1994.

Leserman, L.D. et al., "Covalent Coupling of Monoclonal Antibodies and Protein A to Liposomes: Specific Interaction with Cells in Vitro and in Vivo", *Loposome Technology*, vol. III, pp. 29–40.

Murphy, L. et al., accession No. T34584, 1998.

Nielsen, E. et al., Cysteine Residue Periodicity is a Conserved Structural Feature of Variable Surface Proteins from *Paramecium tetraurelia*, *J. of Mol. Biol.*, vol. 222, pp. 835–841, 1991.

Phillips, M.A. et al., "Genomic Structure of Keratinocyte Transglutaminase", *The Journal of Biological Chemistry*, vol. 267, No. 4, pp. 2282–2286, 1992.

Redenbach, M. et al., "A Set of Ordered Cosmids and a Detalled Genetic and Phisical Map for the 8 Mb Streptomyces coelicolor A3(2) Chromosome", *Molecular Microbiology*, vol. 21, No. 1, pp. 77–96, 1996.

FIBRIN BINDING MOIETIES USEFUL AS IMAGING AGENTS

CROSS-REFERENCE TO RELATED APPLICATION

This application claims priority under 35 U.S.C. 119(e) to provisional application Ser. No. 60/367,373, filed 23 Dec. 2000, now abandoned incorporated by reference herein.

FIELD OF THE INVENTION

The present invention relates to fibrin-binding polypeptides and compositions for detection and treatment of pathological intravascular thrombosis. More particularly, the invention relates to materials useful for and methods of detecting, imaging, and localizing thrombi. The invention provides binding moieties capable of distinguishing between fibrin and circulating fibrinogen and that exhibit a comparatively low dissociation rate from fibrin. Such slow-dissociating binding moieties lead to a longer residence time of bound moieties at the site of a thrombus and an increased signal in comparison to unbound moieties which are cleared quickly from circulation, thereby improving the accuracy and definition of the detected image of a fibrin thrombus. Such binding moieties are useful for the detection, imaging and localization of fibrin-containing clots by magnetic resonance imaging, radioimaging, and other imaging methods and are also useful in the diagnosis and treatment of coronary conditions where fibrin plays a role.

BACKGROUND OF THE INVENTION

Thrombus associated diseases are vascular conditions that are developed due to the presence of a clot. Such diseases are a major cause of mortality, and therefore developing thrombus-specific diagnosis, treatment, and detection methodologies and reagents is of great clinical importance. Pulmonary embolism (PE), deep-vein thrombosis, stroke, and atherosclerosis are examples of thrombus associated diseases.

Deep-vein thrombosis is a condition in which blood clots form in the deep blood vessels of the legs and groin. These clots can block the flow of blood from the legs back to the heart. Sometimes, a piece of a clot is detached and carried by the bloodstream through the heart to a blood vessel, where it lodges and reduces, or blocks, the flow of blood to a vascular tissue. This is called an embolism. Such a clot lodging in a blood vessel in the lung is a pulmonary embolism, or PE. PE can cause shortness of breath, chest pain, or even death.

In the United States alone, there are an estimated 600,000 patients that suffer pulmonary embolism each year. In approximately 378,000 of these patients, PE goes undetected, and approximately 114,000 of these patients die later due to complications associated with the disease. This high mortality is partly due to the absence of clinical symptoms in many cases and to the significant limitations associated with currently available methods of investigation and detection.

There is a need, therefore, for sensitive and effective assays to detect the presence of thromboembolism at various stages of development, for ways to diagnose the presence or absence of early and late thrombi, and for non-invasive reagents that can specifically bind thrombi and which will be useful for detecting the presence or absence of the early or late thrombus in patients.

Thrombus Formation

Crosslinked fibrin forms the underlying backbone of both venous and arterial clots or thrombi (Harker et al., *Am. J. Cardiology*, 60:20B–28B (1987)). Thrombi are formed when the enzyme thrombin is activated, leading to cleavage of plasma fibrinogen to release fibrinopeptides and expose a fibrin polymerization site (Hermans et al., *Semin. Thromb. Hemost.*, 8:11–24 (1982)).

The biology of fibrin and clot formation has been investigated by many researchers in recent years, and a detailed understanding of the cascade of events leading to clot formation has emerged. There are two major activation pathways for coagulation: the intrinsic pathway which requires Factors XII, IX and VIII and the extrinsic pathway which involves tissue factor and Factor VII. Both pathways converge at the point of activating Factor X, the enzyme responsible for converting prothrombin to thrombin.

The extrinsic pathway is initiated by tissue factor, a ubiquitous cellular lipoprotein which forms a calcium-dependent complex with Factor VII. Upon complex formation, Factor VII is activated to Factor VIIa, which converts Factor X to Factor Xa. Factor Xa converts prothrombin to thrombin in conjunction with Factor Va, calcium and phospholipid. Prothrombin conversion also occurs on endothelial surfaces and activated platelets, and requires the assembly of a complex between Factor Xa, Factor Va, and prothrombin. This conversion requires the presence of phospholipid and calcium ions.

The intrinsic or contact coagulation pathway is initiated by platelets. The cascade begins with the formation of a complex among Factor XII, high molecular weight kininogen, and prekallikrein. Upon complex formation, Factor XII is cleaved to Factor XIIa. After the stepwise activation of Factors XI, IX, VIII, X, and V, as in the extrinsic pathway, prothrombin is activated to thrombin. Thrombin, which is a trypsin-like serine protease, is the central regulator of hemostasis and thrombosis. Fibrin is derived from fibrinogen, and polymerization of fibrin occurs following enzymatic cleavage of fibrinogen by thrombin. Fibrinogen (340 kD) consists of three pairs of identical peptides, designated Aα, Bβ, and γ. Chemical structural analysis and electron microscopy have demonstrated that the protein has a trinodular structure. Two AαBβγ subunits are oriented in an antiparallel configuration. The amino terminal portions of the six chains are bundled together in a central "E" domain. Two coiled-coil strands extend outward from either side of the E domain to the two terminal nodes, the "D" domains. These coiled coil regions are 110 amino acids long and composed of all three chains. The D domains contain two high affinity $Ca^{2+}$ binding sites and are involved with the E domain in fibrin polymerization. Extensive disulfide bridges covalently crosslink the two subunits, and stabilize the globular domains. The C-terminal portions of the Aα chains form flexible extensions beyond the D domains. The D domain contains Factor XIIIa crosslinking sites and is the primary site of plasmic digestion during fibrinolysis.

Fibrin formation from fibrinogen is a spontaneous self-assembly process resulting from the removal of fibrinopeptides by thrombin. Thrombin cleavage at the Arg16-Arg17 bond in the Aα chains and at the Arg14-Gly15 bond on the Bβ chains releases fibrinopeptides A and B, and exposes a polymerization site in the E domain consisting mainly of the N-terminus of the α chain. This N-terminus, which bears the sequence Gly-Pro-Arg-Val, binds to a complementary polymerization site on two adjacent fibrinogen chains. End to end association of these fibrinogen molecules mediated by the D domains, creates a binding site for the E domain polymerization site, located on a third fibrinogen molecule. This DD(E) ternary complex forms a core that stabilizes the forming fibrin gel. The initial polymerization product is a linear, two-stranded protofibril. Lateral coalescence of these protofibrils results in thick fibers and a branched, three dimensional matrix. Lateral assembly is complex but probably involves the B polymerization site (the N-terminus of β) and trimolecular complexes formed through D domain interactions.

Adjacent fibrin monomers within the fibrils become covalently crosslinked by Factor XIIIa, a plasma transglutaminase which is itself activated by thrombin and fibrin. These crosslinks add mechanical stability to the fibrin network and increase resistance to clot degradation. Factor XIIIa also enhances clot stability by crosslinking specialized proteins to fibrin, including the plasmin inhibitor $\alpha_2$ antiplasmin, and the adhesion protein fibronectin.

Thrombus Imaging

The search for thrombus-specific imaging agents began three decades ago when radiolabeled fibrinogen was first evaluated (Kakkar et al., *Lancet*, 1:540–542 (1970)). Since then a number of thrombus imaging agents have been described, including agents that are incorporated into forming thrombi and agents that bind to components of previously formed thrombi (Knight et al., *Radiology*, 156:509–514 (1985); Alavi et al., *Radiology*, 175:79–85 (1990); Rosebrough et al., *J. Nuc. Med.* 31:1048–1054 (1990)). Among the recent approaches that have been taken in the development of materials useful for visualizing or imaging thrombi are radiolabeled platelets and anti-platelet antibodies that bind to forming thrombi, anti-fibrin antibodies, anti-activated platelet antibodies, and activated or inactivated tissue type plasminogen activator (tPA) (Thakur et al., *Throm. Res.*, 9:345–357 (1976); Palabrica et al., *Proc. Natl. Acad. Sci.*, 86:1036–1040 (1989)).

Platelet affinity peptides have also been used to detect clots. This approach utilizes small $^{99m}$Tc-labeled peptides capable of binding to platelets. The platelets, with labeled peptide attached, become incorporated into thrombi and render the thrombi detectable (Bautovich et al., *J. Nucl. Med.*, 35:195–202 (1994); Muto et al., *Radiology*, 189 (suppl):303(1993)).

Because platelets in thrombi degrade over time, the use of platelet affinity peptides, anti-platelet antibodies and other agents that bind to platelets or that detect platelet location are only useful for detection of early clots (less than 12 hours) and cannot be used in detection and imaging of embolism, particularly pulmonary embolism.

Since Fibrin is the major protein component in thrombi it is thus a desirable target for agents that can mark the location and gauge the size of a clot in a subject. Fibrin targeting, however, is complicated by the close structural similarity between fibrin and its circulating precursor, fibrinogen. One successful approach has involved the isolation of monoclonal antibodies specific to fibrin. One such class of monoclonals recognizes the newly exposed N-termini of the α and β chains of the fibrin monomers. Another class of monoclonal antibodies recognizes epitopes exposed as a result of polymerization, such as the covalent crosslinks formed by Factor XIII, the DD dimer domain, or the putative tPA binding site. The use of antibodies as imaging agents does, however, have some disadvantages: The high molecular weight of antibodies necessitates that a larger mass of agent must be delivered to a clot than would be required of a small molecule, and this may be a serious limitation when higher concentrations of an imaging agent are essential to obtaining adequate signal contrast. Labeled antibodies often present clearance problems because of relatively long circulating half-lives in vivo, limiting contrast with the blood and tissue background. In addition, antibodies are often expensive to prepare and formulate, and their use can lead to undesirable and potentially fatal immunogenic responses.

Another method used for pulmonary embolism diagnosis is the ventilation/perfusion scan. In a ventilation/perfusion scan, the patient inhales a radiographic gas, and images of regions of the lung that are capable of ventilation are recorded. Subsequently, the patient is injected with a radioactive agent and the movement of the agent through the pulmonary artery is traced. The two images are compared, and any area of thrombosis is detected by contrasting the ventilation data with the perfusion data. Approximately 930,000 ventilation/perfusion scans are performed every year in the United States, but approximately 60% are inconclusive.

An alternate method for pulmonary embolism diagnosis is x-ray angiography. This method is performed by introducing an x-ray opaque (radiopaque) compound proximally to the heart or pulmonary artery via arterial catheter introduced through the patient's femoral vein. The compound is traced through the pulmonary artery by an x-ray camera and thrombosis is detected by such tracing. Although this method is considered a "gold standard" test by clinicians and approximately 60,000 angiographies are performed annually in the United States, the test is invasive and expensive. Moreover, 1 out of 200 patients undergoing the x-ray angiography dies as a direct result of the procedure itself.

Recently, fibrin binding polypeptides have been discovered that are useful, when detectably labeled (e.g., with a paramagnetic metal or radionuclide), as imaging agents for localization and imaging of fibrin clots. See, PCT/US00/20612, incorporated herein by reference. Such fibrin binding polypeptides represent a much needed advance in the art, however there is additional room for improvement in features such as the avidity of the polypeptides for fibrin substrates.

A group of polypeptides has now been discovered which bind to fibrin and also exhibit a low "off-rate", that is, they have a lower dissociation rate than previously characterized binding moieties for fibrin. Such slow-dissociating fibrin binding polypeptides will concentrate at the sites of fibrin clots and remain there longer in comparison to freely circulating such polypeptides, which means that after administration to a patient the circulating polypeptides unbound to fibrin will be cleared from circulation and the remaining polypeptide in a patient's system will be primarily polypeptide that is bound to fibrin. Thus, interfering background signal attributable to circulating labeled polypeptide is cleared and labeled polypeptide at the site of a clot remains, creating a better detectable signal for localization and imaging of a clot.

The newly discovered fibrin binding polypeptides have amino acid sequences differing from previously described fibrin binding moieties. The preparation and use of such polypeptides, for example as imaging agents or as fusion partners for fibrin-homing therapeutics, is described in detail herein.

SUMMARY OF THE INVENTION

In answer to the need for improved materials and methods for detecting, localizing, measuring and treating fibrin clots, we have now surprisingly discovered a group of non-naturally occurring polypeptides that bind specifically to fibrin. Appropriate labeling of such polypeptides provides detectable imaging agents that bind at high concentration to a clot, providing excellent thrombus specific imaging agents. Conjugation or fusion of such polypeptides with effective agents such as thrombolytics can be used to treat thrombotic conditions, e.g., by causing the conjugate or fusion to "home" to the site of a fibrin clot, thereby providing an effective treatment for thrombus associated diseases. Recombinant bacteriophage or yeast cells, mammalian cells, insect cells, or other prokaryotic or eukaryotic cells displaying the fibrin-binding polypeptides of the invention are provided, and such phage and cellular products are also valuable reagents for effective detection and diagnosis of thrombi.

In addition to the detection of thromboembolism and thrombus formation, e.g., on atherosclerotic plaque, the newly discovered fibrin binders can also be used advantageously to detect numerous other pathophysiologies in which fibrin plays a role. In these cases, fibrin imaging can be a useful direct or surrogate marker for diagnosis or therapeutic monitoring. For example, peritoneal adhesions often occur after surgery or inflammatory and neoplastic processes, and are comprised of a fibrin network, fibroblasts, macrophages, and new blood vessels. Patients suffering from rheumatoid arthritis, lupus, or septic arthritis often have bits of fibrin-containing tissues called rice bodies in the synovial fluid of their joints. In thrombotic thrombocytopenic purpura, a type of anemia, fibrin deposits in arterioles cause turbulent blood flow, resulting in stress and destruction of the red blood cells. The fibrin binding moieties of the instant invention can be used in the detection and diagnosis of such fibrin-related disorders.

The fibrin specific agents can also be used to detect other conditions including but not limited to hypoxia or ischemia of the heart, kidney, liver, lung, brain, or other organs, as well as the detection of tumors, diabetic retinopathy, early or high-risk atherosclerosis, and other autoimmune and inflammatory disorders. Fibrin specific agents also could provide both direct or surrogate markers of disease models in which hypoxia and angiogenesis are expected to play a role. In hypoxic conditions, fibrin(ogen) is expressed under the control of hypoxia-inducible factor 1 (HIF-1). In those disease models where angiogenesis plays a role, such as tumor growth and invasion, fibrin provides the structural mesh required for the generation of new blood vessels.

This invention pertains to fibrin binding moieties. Binding moieties according to this invention are useful in any application where binding, detecting or isolating fibrin or its fragments (e.g., DD and DD(E)) is advantageous. A particularly advantageous use of the binding moieties disclosed herein is in a method of imaging thrombi in vivo. The method entails the use of fibrin specific binding moieties according to the invention for detecting a thrombus, where the binding moieties have been detectably labeled for use as imaging agents, including magnetic resonance imaging (MRI) contrast agents, x-ray imaging agents, radiopharmaceutical imaging agents, ultrasound imaging agents, and optical imaging agents.

The most preferred fibrin binding moieties according to the invention are isolated, synthetic polypeptides having a high affinity for fibrin. This invention provides a new class of fibrin binding polypeptides having an amino acid sequence comprising:

$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$ (SEQ ID NO:1), wherein $X_1$ is Cys, Pro, or Trp, preferably Trp;
$X_2$ is Ala, Arg, Asn, Asp, Gln, Glu, Gly, His, Ile, Leu, Lys, Met, Phe, Pro, Ser, Thr, Trp, Tyr or Val (that is, any amino acid except Cys), or if $X_4$ and $X_{12}$ are not Cys, then $X_2$ may be Cys; most preferably $X_2$ is Ala, Gln, Glu, Lys, or Met;
$X_3$ is Ala, Asn, Gln, Gly, Ile, Leu, Met, Phe, Pro, or Thr; most preferably $X_3$ is Ala, Leu, Met, or Pro;
$X_4$ is Cys or another amino acid capable of forming a covalent cross-link to $X_{12}$; most preferably $X_4$ and $X_{12}$ both are Cys;
$X_5$ is Pro, Arg, Asn, Asp, Gln, Gly, Phe, Ser, Thr or Tyr; preferably $X_5$ is Pro;
$X_6$ is Ala, Asn, Asp, Gln, Glu, Gly, Ile, Leu, Met, Phe, Pro, Ser, Thr, Trp, Tyr, or Val; preferably $X_6$ is Asp, Glu, Gly, Met, or Trp;
$X_7$ is Glu, Gly, Lys, Ser, or Tyr, most preferably Glu;
$X_8$ is Pro, Asp, Glu, Asn, Gln, Glu, Gly, Leu, Lys, Ser, Thr, or Tyr; preferably, $X_8$ is Asn, Asp, Glu, Pro, or Ser; most preferably, $X_8$ is Pro;
$X_9$ is Arg, Gly, or Trp, preferably Trp;
$X_{10}$ is Leu, Ile, Lys, Met, Asn, Gln, Pro, Ser, Thr, or Val; preferably $X_{10}$ is Leu or Thr;
$X_{11}$ is Ile, Leu, Phe, Trp, or Tyr;
$X_{12}$ is Cys or another amino acid capable of forming a covalent cross-link to $X_4$;
$X_{13}$ is Cys, Gly, Leu, Phe, Pro, Trp, or Tyr, most preferably Trp;
$X_{14}$ is Pro, Ala, Gly, Asn, Gln, Lys, Ser, Thr, Tyr, Asp, Glu, or His; preferably $X_{14}$ is Asp, Gly, His, Phe, or Ser; and
$X_{15}$ is Ala, Arg, Asp, Ile, Leu, Met, Phe, Pro, Trp, Val, Asn, Gln, Gly, Ser, Thr, Tyr, or His; preferably $X_{15}$ is Ala, Gly, His, Pro, or Ser,
wherein said polypeptide has the ability to bind fibrin.

In particular, a stable binding loop having a high affinity for fibrin is disclosed, having the formula: Cys-$X_2$-$X_3$-$X_4$-$X_5$-$X_6$-$X_7$-$X_8$-Cys (SEQ ID NO: 2), wherein $X_2$ is Pro, Arg, Asn, Asp, Gln, Gly, Phe, Ser, Thr, or Tyr; preferably $X_2$ is Pro;
$X_3$ is Ala, Asn, Asp, Gln, Glu, Gly, Lle, Leu, Met, Phe, Pro, Ser, Thr, Trp, Tyr, or Val; preferably $X_3$ is Asp, Glu, Gly, Met, or Trp;
$X_4$ is Glu, Gly, Lys, Ser, or Tyr; most preferably Glu;
$X_5$ is Pro, Asp, Glu, Asn, Gln, Gly, Leu, Lys, Ser, Thr, or Tyr; preferably $X_5$ is Asn, Asp, Glu, Pro, or Ser; most preferably $X_5$ is Pro;
$X_6$ is Mrg, Gly, or Trp;
$X_7$ is Leu, Ile, Lys, Met, Asn, Gln, Pro, Ser, Thr, or Val; preferably $X_7$ is Leu or Thr; and
$X_8$ is Ile, Leu, Phe, Trp, or Tyr.

Particularly preferred fibrin binding moieties according to the invention are polypeptides including the amino acid sequences:

Trp-Glu-Leu-Cys-Ser-Asp-Glu-Asn-Trp-Leu-Trp-Cys-Trp-Pro-His (SEQ ID NO: 3),
Trp-Met-Met-Cys-Pro-Met-Ser-Glu-Trp-Leu-Tyr-Cys-Trp-Ser-Ala (SEQ ID NO: 4),
Trp-Gln-Pro-Cys-Pro-Trp-Glu-Ser-Trp-Thr-Phe-Cys-Trp-Asp-Pro (SEQ ID NO: 5),
Trp-Ala-Pro-Cys-Gln-Glu-Glu-Pro-Trp-Leu-Phe-Cys-Phe-His-Gly (SEQ ID NO: 6),
Trp-Lys-Ala-Cys-Pro-Gly-Glu-Asp-Trp-Leu-Phe-Cys-Trp-Gly-Ser (SEQ ID NO: 7), and
Arg-Ala-Pro-Cys-Asp-Tyr-Tyr-Gly-Thr-Cys-Val-Glu-Leu (SEQ ID NO: 8).

Additional preferred fibrin binding moieties according to the invention are polypeptides including the amino acid sequences:

Pro-Arg-Pro-Cys-Tyr-Gly-Glu-Ser-Gly-Ile-Phe-Cys-Trp-Lys-Val (SEQ ID NO:27);
Pro-Arg-Pro-Cys-Thr-Gly-Glu-Gly-Pro-Gly-Pro-Ile-Cys-Gly-Pro-Arg (SEQ ID NO:28);
Trp-Gln-Ala-Cys-Gln-Leu-Gly-Tyr-Arg-Thr-Tyr-Cys-Trp-Asp-Gly (SEQ ID NO:29);

Trp-Lys-Phe-Cys-Asp-Gly-Glu-Pro-Trp-Leu-Phe-Cys-Trp-Asp-Gly (SEQ ID NO:30);
Trp-Asn-Gly-Cys-Gly-Trp-Gly-Ser-Trp-Lys-Phe-Cys-Gly-Glu-Gly (SEQ ID NO:31);
Trp-Leu-Asn-Cys-Gly-Trp-Gly-Ser-Gly-Lys-Leu-Cys-Leu-Gly-Val (SEQ ID NO:32);
Cys-Tyr-Phe-Cys-Pro-Gly-Glu-Pro-Trp-Thr-Phe-Cys-Cys-Asp-Asp (SEQ ID NO:33);
Trp-His-Phe-Cys-Pro-Gly-Glu-Pro-Trp-Thr-Phe-Cys-Trp-Ala-Gly (SEQ ID NO:34);
Trp-Gln-Thr-Cys-Pro-Gly-Tyr-Leu-Arg-Ser-Leu-Cys-Trp-Asp-Gly (SEQ ID NO:35);
Trp-Tyr-Phe-Cys-Pro-Gly-Glu-Pro-Trp-Ser-Phe-Cys-Pro-Asp-Gly (SEQ ID NO:36);
Pro-Arg-Pro-Cys-Arg-Gly-Glu-Ser-Trp-Pro-Tyr-Cys-Trp-Gly-Gly (SEQ ID NO:37);
Trp-Gln-Ala-Cys-Pro-Gly-Tyr-Lys-Arg-Gln-Phe-Cys-Trp-Asp-Arg (SEQ ID NO:38);
Pro-Arg-Pro-Cys-Gly-Gln-Glu-Ser-Arg-Thr-Phe-Cys-Leu-Glu-Gly (SEQ ID NO:39); and
Pro-Arg-Pro-Cys-Phe-Gln-Lys-Gly-Gly-Thr-Leu-Cys-Trp-Pro-Gly (SEQ ID NO:40).

Another aspect of the present invention relates to modifications of the foregoing polypeptides to provide fibrin specific imaging agents by radiolabeling, enzymatic labeling, or labeling with MR paramagnetic chelates or microparticles; incorporation into ultrasound bubbles, microparticles, microspheres, emulsions, or liposomes; or additions including optical dyes.

In another aspect of the present invention, methods for isolating fibrin binding moieties are provided. Such methods will be useful for isolating additional reagents for detection, localization, quantification, and treatment of thrombi.

In another aspect of the invention, methods of detecting fibrin-containing pathophysiologies, including thrombi, are provided, and methods for treating thrombotic diseases are provided.

In another aspect of the invention, therapeutic agents comprising a combination, conjugation or fusion of a thrombolytic agent or other therapeutic with a fibrin binding moiety according to the invention are provided. Such compositions will be useful in the treatment of thrombus associated diseases and conditions.

In another aspect of the invention, recombinant bacteriophage, yeast, mammalian cells, insect cells, or other prokaryotic or eukaryotic cells displaying fibrin binding polypeptides on their surfaces are also provided. Such phage and host cells are useful as screening reagents and reagents for detecting fibrin.

These and other aspects of the present invention will become apparent with reference to the following detailed description.

DEFINITIONS

Figure 1:
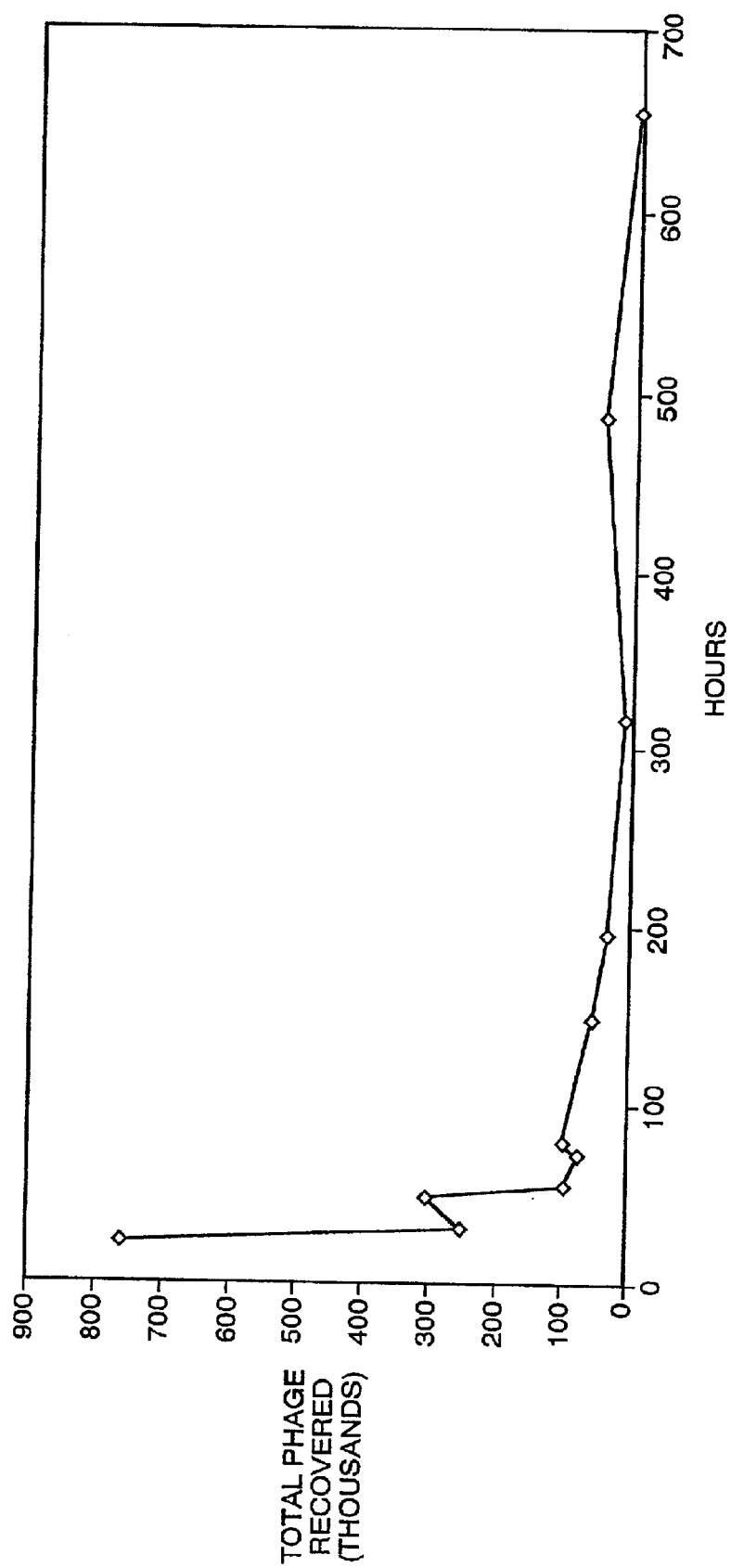
FIG. 1 shows the number of phage isolates collected as a function of kinetic elution time (see Example 4).

In the following sections, the term "recombinant" is used to describe non-naturally altered or manipulated nucleic acids, host cells transfected with exogenous nucleic acids, or polypeptides expressed non-naturally, through manipulation of isolated DNA and transformation of host cells. Recombinant is a term that specifically encompasses DNA molecules which have been constructed in vitro using genetic engineering techniques, and use of the term "recombinant" as an adjective to describe a molecule, construct, vector, cell, polypeptide or polynucleotide specifically excludes naturally occurring such molecules, constructs, vectors, cells, polypeptides or polynucleotides.

As used herein, the term "fibrin-derived polypeptide" refers to any subcomponent of fibrin or fragment of fibrin that is immunologically cross-reactive with fibrin, including immunologically reactive fragments of the protein.

The term "bacteriophage" is defined as a bacterial virus containing a DNA core and a protective shell built up by the aggregation of a number of different protein molecules. The terms "bacteriophage" and "phage" are used herein interchangeably. Unless otherwise noted, the terms "bacteriophage" and "phage" also encompass "phagemids" (i.e., bacteriophage the genome of which includes a plasmid that can be packaged by coinfection of a host with a helper phage) as well known by practitioners in the art. In preferred embodiments of the present invention, the phage is an M13 phage.

The term "polypeptide" is used to refer to a compound of two or more amino acids joined through the main chain (as opposed to side chain) by a peptide amide bond (—C(:O)NH—). The term "peptide" is used interchangeably herein with "polypeptide" but is generally used to refer to polypeptides having fewer than 25 amino acids.

The term "binding moiety" as used herein refers to any molecule capable of forming a binding complex with another molecule. "Fibrin binding moiety" is a binding moiety that forms a complex with a clot, soluble or insoluble fibrin, or a soluble or insoluble fragment of fibrin having a structure or characteristic exhibited by fibrin but not fibrinogen. Included among such soluble or insoluble fragments of fibrin are fragments defined as "fibrin-derived" polypeptides. Fibrin-derived polypeptides, for the purposes of this invention will be used as a collective term for the DD, DD-dimer, and DD(E) polypeptides described herein. Such fibrin-derived polypeptides are typically generated by proteolytic treatment of crosslinked fibrin but retain structural features unique to fibrin. Specific examples of fibrin binding moieties are the polypeptides described herein (including, for example, SEQ ID NOs: 1–8 and 27–40), hybrid and chimeric polypeptides incorporating such polypeptides, and recombinant cells or bacteriophage displaying any of such polypeptides. Also included within the definition of fibrin binding moieties are polypeptides which are modified as disclosed herein. Specific examples of modifications are C- or N-terminal amino acid substitutions or elongations, e.g., for the purpose of linking the binding moiety to a detectable imaging label or other substrate, examples of which include, e.g., addition of a polyhistidine "tail" in order to assist in purification; substitution of one up to several amino acids in order to obliterate an enzyme cleavage site; the use of N-terminal or C-terminal modifications or linkers, such as polyglycine or polylysine segments; alterations to include functional groups, notably hydrazide (—NH—NH$_2$) functionalities, to assist in immobilization of binding peptides according to this invention on solid supports; and the like. In addition to the detectable labels described further herein, other suitable substrates for the fibrin binding polypeptides include a thrombolytic agent or enzyme (e.g., tPA, plasmin, streptokinase, urokinase, hirudin), a liposome (e.g., loaded with thrombolytic agent, an ultrasound appropriate gas or both), or a solid support, well, plate, bead, tube, slide, filter, or dish. All such modified fibrin binding moieties are also considered fibrin binding moieties so long as they retain the ability to bind fibrin or fibrin-derived polypeptides.

The terms "DD", "DD dimer", and "DD(E)" refer to fibrin subcomponents typically generated by proteolytic degradation of fibrin with plasmin or trypsin. The terms "DD" and "DD dimer" both refer to the glutaminase crosslinked D domains of adjacent fibrin monomers, about 180 kDa in molecular weight. The term "DD dimer" encompasses the C-terminal portion of fibrin, including roughly $\alpha(111–197)$, $\beta(134–461)$ and $\gamma(88–406)$ in the human fibrinogen sequence. The term "DD(E)" refers to a complex of DD with the central E domain of fibrin, about 60 kDa in molecular weight, and roughly includes $\alpha(111–197)$, $\beta(134–461)$, $\gamma(88–406)$, $\alpha(17–78)$, $\beta(15–122)$ and $\gamma(1–62)$ in the human fibrinogen sequence. Since "DD" and "DD(E)" are products of proteolysis of fibrin, there may be some slight heterogeneity in their composition, depending on the mode of protease digestion and their subsequent isolation. (See, Olexa et al., *Biochemistry*, 20: 6139–6145 (1981); Moskowitz and Budzynski, *Biochemistry*, 33: 12937–12944 (1994); Spraggon et al., *Nature*, 389: 455–462 (1997); and references therein.)

The term "binding" refers to the determination by standard assays, including those described herein, that a binding moiety recognizes and binds reversibly to a given target. Such standard assays include equilibrium dialysis, gel filtration, and the monitoring of spectroscopic changes that result from binding.

The term "specificity" refers to a binding moiety having a higher binding affinity for one target over another. The term "fibrin specificity" refers to a fibrin binding moiety having a higher affinity for fibrin over fibrinogen. Fibrin specificity may be characterized by a dissociation equilibrium constant ($K_D$) or an association equilibrium constant ($K_a$) for the two tested materials. The binding polypeptides according to the present invention have a rate of dissociation from fibrin that is lower than previously known fibrin binding polypeptides. $k_{off}$ is the first-order rate constant for dissociation of the fibrin/fibrin-binding-moiety complex. $k_{on}$ is the second-order rate constant for the formation of the fibrin/fibrin-binding-moiety complex. The dissociation equilibrium constant is related to the rate constants as $K_D = k_{off}/k_{on}$, thus a lower $K_D$ correlates with but does not guarantee a lower $k_{off}$. Binding moieties according to the present invention preferably will have a lower dissociation rate than previously isolated binding polypeptides.

The term "patient" as used herein refers to any mammal, especially humans.

The term "pharmaceutically acceptable" carrier or excipient refers to a non-toxic carrier or excipient that may be administered to a patient, together with a compound of this invention, and which does not destroy the pharmacological activity thereof.

DETAILED DESCRIPTION OF THE INVENTION

The present invention provides novel binding moieties for fibrin. Such binding moieties make possible the efficient detection, imaging and localization of fibrin or fibrin-derived peptides in a solution or system that contains fibrin or fibrin-derived polypeptides. In particular, the binding moieties of this invention, when appropriately labeled, are useful for detecting, imaging and localizing fibrin-containing thrombi or other fibrin specific pathophysiologies, and can thus be used to form a variety of diagnostic and therapeutic agents for diagnosing and treating thrombotic disease. The preferred binding moieties of the present invention bind fibrin and/or fibrin-derived polypeptides with high affinity, i.e., acting at low, physiologically relevant concentrations, comparable to known anti-fibrin antibodies and other fibrin-binding proteins.

Specific fibrin binding polypeptides according to the present invention were isolated initially by screening of phage display libraries, that is, populations of recombinant bacteriophage transformed to express an exogenous peptide loop on their surface. In order to isolate new polypeptide binding moieties for a particular target, such as fibrin, screening of large peptide libraries, for example using phage display techniques, is especially advantageous, in that very large numbers (e.g., $5 \times 10^9$) of potential binders can be tested and successful binders isolated in a short period of time.

In order to prepare a phage library of potential polypeptides to screen for binding moieties such as fibrin binding peptides, a candidate binding domain is selected to serve as a structural template for the peptides to be displayed in the library. The phage library is made up of a multiplicity of analogues of the parental domain or template. The binding domain template may be a naturally occurring or synthetic protein, or a region or domain of a protein. The binding domain template may be selected based on knowledge of a known interaction between the binding domain template and fibrin, but this is not critical. In fact, it is not essential that the domain selected to act as a template for the library have any affinity for the target at all: Its purpose is to provide a structure from which a multiplicity (library) of similarly structured polypeptides (analogues) can be generated, which multiplicity of analogues will hopefully include one or more analogues that exhibit the desired binding properties (and any other properties screened for).

In selecting the parental binding domain or template on which to base the variegated amino acid sequences of the library, the most important consideration is how the variegated peptide domains will be presented to the target, i.e., in what conformation the peptide analogues will come into contact with the target. In phage display methodologies, for example, the analogues will be generated by insertion of synthetic DNA encoding the analogues into phage, resulting in display of the analogue on the surfaces of the phage. Such libraries of phage, such as M13 phage, displaying a wide variety of different polypeptides, can be prepared using techniques as described, e.g., in Kay et al., *Phage Display of Peptides and Proteins: A Laboratory Manual* (Academic Press, Inc., San Diego 1996) and U.S. Pat. No. 5,223,409 (Ladner et al.), incorporated herein by reference.

For formation of phage display libraries, it is preferred to use a structured polypeptide as the binding domain template, as opposed to an unstructured, linear peptide. Mutation of surface residues in a protein will usually have little effect on the overall structure or general properties (such as size, stability, and temperature of denaturation) of the protein; while at the same time mutation of surface residues may profoundly affect the binding properties of the protein. The more tightly a polypeptide segment is constrained, the less likely it is to bind to any particular target, however if the polypeptide does bind, the binding is likely to be of higher affinity and of greater specificity. Thus, it is preferred to select a parental domain and, in turn, a structure for the potential polypeptide binders, that is constrained within a framework having some degree of rigidity. In isolating the specific polypeptides according to this invention, three libraries designated TN7/IV, TN8/IX, and TN9/IV (each having greater than $2\times10^9$ amino acid sequence diversity) was used. Each library was constructed for expression of diversified polypeptides on M13 phage. The TN7/IV library was constructed to display a single polypeptide binding loop contained in an 13-amino acid template. The TN7/IV library utilized a template sequence of Xaa-Xaa-Xaa-Cys-Xaa-Xaa-Xaa-Xaa-Xaa-Cys-Xaa-Xaa-Xaa (SEQ ID NO: 9). The TN8/IX library was constructed to display a single polypeptide binding loop contained in an 14-amino acid template. The TN8/IX library utilized a template sequence of Xaa-Xaa-Xaa-Cys-Xaa-Xaa-Xaa-Xaa-Xaa-Xaa-Cys-Xaa-Xaa-Xaa (SEQ ID NO:10). The TN9/IV library was constructed to display a single polypeptide binding loop contained in an 15-amino acid template. The TN9/IV library utilized a template sequence of Xaa-Xaa-Xaa-Cys-Xaa-Xaa-Xaa-Xaa-Xaa-Xaa-Xaa-Cys-Xaa-Xaa-Xaa (SEQ ID NO:11).

Such small binding loop peptides offer several advantages over large proteins: First, the mass per binding site is reduced, e.g., such highly stable and low molecular weight polypeptide domains can show much higher binding per gram than do antibodies (150 kDa) or single-chain antibodies (30 kDa). Second, the possibility of non-specific binding is reduced because there is less surface available. Third, small proteins or polypeptides can be engineered to have unique tethering sites such as terminal polylysine segments in a way that is impracticable for larger proteins or antibodies. Fourth, a constrained polypeptide structure is more likely to retain its functionality when transferred with the structural domain intact from one framework to another, that is, the binding domain structure is likely to be transferable from the framework used for presentation in a library (e.g., displayed on a phage) to an isolated protein removed from the presentation framework or immobilized on a chromatographic substrate.

The TN7, TN8 and TN9 libraries were created by making a designed series of mutations or variations within a coding sequence for the polypeptide template, each mutant sequence encoding a binding loop analogue corresponding in overall structure to the template except having one or more amino acid variations in the sequence of the template. The novel variegated (mutated) DNA provides sequence diversity, and each transformant phage displays one variant of the initial template amino acid sequence encoded by the DNA, leading to a phage population (library) displaying a vast number of different but structurally related amino acid sequences. The amino acid variations are expected to alter the binding properties of the binding loop or domain without significantly altering its structure, at least for most substitutions. It is preferred that the amino acid positions that are selected for variation (variable amino acid positions) will be surface amino acid positions, that is, positions in the amino acid sequence of the domains which, when the domain is in its most stable conformation, appear on the outer surface of the domain (i.e., the surface exposed to solution). Most preferably the amino acid positions to be varied will be adjacent or close together, so as to maximize the effect of substitutions.

As indicated previously, the techniques discussed in Kay et al., *Phage Display of Peptides and Proteins: A Laboratory Manual* (Academic Press, Inc., San Diego 1996) and U.S. Pat. No. 5,223,409 are particularly useful in preparing a library of potential binders corresponding to the selected parental template. The TN7, TN8 and TN9 libraries were prepared according to such techniques, and they were screened for fibrin binding polypeptides against an immobilized fibrin target (e.g., DD(E) fibrin).

In a typical screen, a phage library is contacted with and allowed to bind the target, in this case, fibrin or a particular subcomponent, such as DD(E), presenting structures unique to the polymerized form of fibrin found in clots. To facilitate separation of binders and non-binders, it is convenient to immobilize the target on a solid support. Since fibrin is already insoluble, it is readily adaptable to phage screening. Soluble targets such as DD(E), on the other hand, must be immobilized by chemical modification. Phage bearing a target-binding moiety form a complex with the target on the solid support whereas non-binding phage remain in solution and may be washed away with excess buffer. Bound phage are then liberated from the target by changing the buffer to an extreme pH (pH 2 or pH 10), changing the ionic strength of the buffer, adding denaturants, or other known means. The recovered phage may then be amplified through infection of bacterial cells and the screening process repeated with the new pool that is now depleted in non-binders and enriched in binders. The recovery of even a few binding phage is sufficient to carry the process to completion. After a few rounds of selection, the gene sequences encoding the binding moieties derived from selected phage clones in the binding pool are determined by conventional methods, described below, revealing the peptide sequence that imparts binding affinity of the phage to the target. When the selection process works, the sequence diversity of the population falls with each round of selection until desirable binders remain. The sequences converge on a small number of related binders, typically 10–50 out of the more than 10 million original candidates. An increase in the number of phage recovered at each round of selection, and of course, the recovery of closely related sequences are good indications that convergence of the library has occurred in a screen.

After a set of binding polypeptides is identified, the sequence information may be used to design other secondary phage libraries, biased for members having additional desired properties. Such a secondary library was designed around a fibrin binding polypeptide isolated from the TN9/IV library (see, Example 6, infra).

In the screening for slow-dissociation rate fibrin binders performed as described herein, only the TN7/IV and the TN9/IV libraries gave fibrin binding polypeptides having a relatively low off. Because the TN9/IV library yielded a number of slowly dissociating fibrin binders, the sequences were carefully analyzed to determine the range or type of amino acids that would be suitable at each amino acid position, in order to define a family of particular fibrin binders, comprising the following amino acid sequence corresponding to the template of the TN9/IV library:

Trp-$X_2$-$X_3$-$X_4$-$X_5$-$X_6$-$X_7$-$X_8$-Trp-$X_{10}$-$X_{11}$-$X_{12}$-$X_{13}$-$X_{14}$-$X_{15}$ (SEQ ID NO:41), wherein $X_2$ may be Ala, Arg, Asn, Asp, Gln, Glu, Gly, His, Ile, Leu, Lys, Met, Phe, Pro, Ser, Thr, Trp, Tyr or Val (that is, any amino acid except Cys, which would destabilize the disulfide formation between $X_4$ and $X_{12}$), or if $X_4$ and $X_{12}$ are not Cys, then $X_2$ may be Cys; most preferably $X_2$ is Ala, Gln, Glu, Lys, or Met;

$X_3$ is any uncharged amino acid except Cys, i.e., $X_3$ is picked from the group Ala, Asn, Gln, Gly, Ile, Leu, Met, Phe, or Pro; most preferably $X_3$ is Ala, Leu, Met, or Pro;

$X_4$ is Cys or another amino acid capable of forming a covalent cross-link to $X_{12}$; most preferably $X_4$ and $X_{12}$ both are Cys;

X₅ is either Pro or a small, uncharged, polar amino acid, i.e, is Asn, Gln, Ser, or Thr; preferably X₅ is Pro;

X₆ is any non-basic amino acid but not Cys, i.e., is Ala, Asn, Asp, Gln, Glu, Gly, Ile, Leu, Met, Phe, Pro, Ser, Thr, Trp, Tyr, or Val; preferably X₆ is Asp, Glu, Gly, Met, or Trp;

X₇ is Glu or Ser, most preferably Glu;

X₈ is Pro, or an acidic amino acid (i.e., Asp or Glu), or an amino acid having an uncharged polar side chain, other than Cys (i.e., Asn, Gln, Ser, Thr, Tyr); preferably, X₈ is Asn, Asp, Glu, Pro, or Ser; most preferably, X₈ is Pro;

X₁₀ is an amino acid other than Cys and having an aliphatic uncharged polar or aliphatic nonpolar (hydrophobic) side chain (i.e., X₁₀ is Leu, Ile, Met, Asn, Gln, Ser, Thr, or Val); preferably X₁₀ is Leu or Thr;

X₁₁ is an aromatic hydrophobic amino acid (i.e., X₁₁ is Phe, Trp, or Tyr);

X₁₂ is Cys or another amino acid capable of forming a covalent cross-link to X₄;

X₁₃ is an aromatic hydrophobic amino acid (i.e., X₁₃ is Phe, Trp, or Tyr), most preferably Trp;

X₁₄ is Pro or a small amino acid (i.e., Ala or Gly), a polar uncharged amino acid other than Cys (i.e., Asn, Gln, Ser, Thr or Tyr), an acidic amino acid (i.e., Asp or Glu), or a weakly basic amino acid (i.e., His); preferably X₁₄ is Asp, Gly, His, Phe, or Ser; and X₁₅ is a nonpolar amino acid (i.e., Ala, Ile, Leu, Met, Phe, Pro, Trp, or Val), an uncharged polar amino acid other than Cys (i.e., Asn, Gln, Gly, Ser, Thr, or Tyr), or a weakly basic amino acid (i.e., His); preferably X₁₅ is Ala, Gly, His, Pro, or Ser.

Particularly preferred examples of such polypeptides include:

Trp-Glu-Leu-Cys-Ser-Asp-Glu-Asn-Trp-Leu-Trp-Cys-Trp-Pro-His (SEQ ID NO: 3),

Trp-Met-Met-Cys-Pro-Met-Ser-Glu-Trp-Leu-Tyr-Cys-Trp-Ser-Ala (SEQ ID NO: 4),

Trp-Gln-Pro-Cys-Pro-Trp-Glu-Ser-Trp-Thr-Phe-Cys-Trp-Asp-Pro (SEQ ID NO: 5),

Trp-Ala-Pro-Cys-Gln-Glu-Glu-Pro-Trp-Leu-Phe-Cys-Phe-His-Gly (SEQ ID NO: 6), and

Trp-Lys-Ala-Cys-Pro-Gly-Glu-Asp-Trp-Leu-Phe-Cys-Trp-Gly-Ser (SEQ ID NO: 7).

A single TN7 binder was isolated, having the sequence: Arg-Ala-Pro-Cys-Asp-Tyr-Tyr-Gly-Thr-Cys-Val-Glu-Leu (SEQ ID NO: 8).

The cysteine residues of these polypeptides are believed to form a disulfide bond, which causes the polypeptide to form a stable loop or cyclic structure under non-reducing conditions. Thus, the invention relates to the discovery of a fibrin binding loop comprising a polypeptide comprising the amino acid sequence: Cys-X₂-X₃-X₄-X₅-Trp-X₇-X₈-Cys (SEQ ID NO: 42), wherein X₂ is Pro, Asn, Gln, Ser, or Thr, preferably Pro;

X₃ is Ala, Asn, Asp, Gln, Glu, Gly, Ile, Leu, Met, Phe, Pro, Ser, Thr, Trp, Tyr, or Val, preferably Asp, Glu, Gly, Met, or Trp;

X₄ is Glu or Ser, preferably Glu;

X₅ is Pro, Asp, Glu, Asn, Gln, Ser, Thr, or Tyr, preferably Asn, Asp, Glu, Pro, or Ser, most preferably Pro;

X₇ is Leu, Ile, Met, Asn, Gln, Ser, Thr, or Val, preferably Leu or Thr; and

X₈ is Phe, Trp, or Tyr, preferably Phe.

The fibrin binding loop of the TN7 isolate is: Cys-Asp-Tyr-Tyr-Gly-Thr-Cys (SEQ ID NO: 12).

Creation of a secondary library based on a particular fibrin binding polypeptide and selection for slow dissociation binders led to the isolation of additional fibrin binding polypeptides:

Pro-Arg-Pro-Cys-Tyr-Gly-Glu-Ser-Gly-Ile-Phe-Cys-Trp-Lys-Val (SEQ ID NO:27);

Pro-Arg-Pro-Cys-Thr-Gly-Glu-Pro-Gly-Pro-Ile-Cys-Gly-Pro-Arg (SEQ ID NO:28);

Trp-Gln-Ala-Cys-Gln-Leu-Gly-Tyr-Arg-Thr-Tyr-Cys-Trp-Asp-Gly (SEQ ID NO:29);

Trp-Lys-Phe-Cys-Asp-Gly-Glu-Pro-Trp-Leu-Phe-Cys-Trp-Asp-Gly (SEQ ID NO:30);

Trp-Asn-Gly-Cys-Gly-Trp-Gly-Ser-Trp-Lys-Phe-Cys-Gly-Glu-Gly (SEQ ID NO:31);

Trp-Leu-Asn-Cys-Gly-Trp-Gly-Ser-Gly-Lys-Leu-Cys-Leu-Gly-Val (SEQ ID NO:32);

Cys-Tyr-Phe-Cys-Pro-Gly-Glu-Pro-Trp-Thr-Phe-Cys-Cys-Asp-Asp (SEQ ID NO:33);

Trp-His-Phe-Cys-Pro-Gly-Glu-Pro-Trp-Thr-Phe-Cys-Trp-Ala-Gly (SEQ ID NO:34);

Trp-Gln-Thr-Cys-Pro-Gly-Tyr-Leu-Arg-Ser-Leu-Cys-Trp-Asp-Gly (SEQ ID NO:35);

Trp-Tyr-Phe-Cys-Pro-Gly-Glu-Pro-Trp-Ser-Phe-Cys-Pro-Asp-Gly (SEQ ID NO:36);

Pro-Arg-Pro-Cys-Arg-Gly-Glu-Ser-Trp-Pro-Tyr-Cys-Trp-Gly-Gly (SEQ ID NO:37);

Trp-Gln-Ala-Cys-Pro-Gly-Tyr-Lys-Arg-Gln-Phe-Cys-Trp-Asp-Arg (SEQ ID NO:38);

Pro-Arg-Pro-Cys-Gly-Gln-Glu-Ser-Arg-Thr-Phe-Cys-Leu-Glu-Gly (SEQ ID NO:39); and

Pro-Arg-Pro-Cys-Phe-Gln-Lys-Gly-Gly-Thr-Leu-Cys-Trp-Pro-Gly (SEQ ID NO:40).

Examination of those sequences in comparison to the previously isolated sequences provides an expanded class of fibrin binding polypeptides comprising an amino acid sequence of the formula:

$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$ (SEQ ID NO:1), wherein X₁ is Cys, Pro, or Trp, preferably Trp;

X₂ is Ala, Arg, Asn, Asp, Gln, Glu, Gly, His, Ile, Leu, Lys, Met, Phe, Pro, Ser, Thr, Trp, Tyr or Val (that is, any amino acid except Cys), or if X₄ and X₁₂ are not Cys, then X₂ may be Cys; most preferably X₂ is Ala, Gln, Glu, Lys, or Met;

X₃ is Ala, Asn, Gln, Gly, Ile, Leu, Met, Phe, Pro, or Thr; most preferably X₃ is Ala, Leu, Met, or Pro;

X₄ is Cys or another amino acid capable of forming a covalent cross-link to X₁₂; most preferably X₄ and X₁₂ both are Cys;

X₅ is Pro, Arg, Asn, Asp, Gln, Gly, Phe, Ser, Thr or Tyr; preferably X₅ is Pro;

X₆ is Ala, Asn, Asp, Gln, Glu, Gly, Ile, Leu, Met, Phe, Pro, Ser, Thr, Trp, Tyr, or Val; preferably X₆ is Asp, Glu, Gly, Met, or Trp;

X₇ is Glu, Gly, Lys, Ser, or Tyr, most preferably Glu;

X₈ is Pro, Asp, Glu, Asn, Gln, Glu, Gly, Leu, Lys, Ser, Thr, or Tyr; preferably, X₈ is Asn, Asp, Glu, Pro, or Ser; most preferably, X₈ is Pro;

X₉ is Arg, Gly, or Trp, preferably Trp;

X₁₀ is Leu, Ile, Lys, Met, Asn, Gln, Pro, Ser, Thr, or Val; preferably X₁₀ is Leu or Thr;

X₁₁ is Ile, Leu, Phe, Trp, or Tyr;

X₁₂ is Cys or another amino acid capable of forming a covalent cross-link to X₄;

X₁₃ is Cys, Gly, Leu, Phe, Pro, Trp, or Tyr, most preferably Trp;

X₁₄ is Pro, Ala, Gly, Asn, Gln, Lys, Ser, Thr, Tyr, Asp, Glu, or His; preferably X₁₄ is Asp, Gly, His, Phe, or Ser; and X₁₅ is Ala, Arg, Asp, Ile, Leu, Met, Phe, Pro, Trp, Val, Asn, Gln, Gly, Ser, Thr, Tyr, or His; preferably X₁₅ is Ala, Gly, His, Pro, or Ser.

In addition, a stable binding loop having a high affinity for fibrin is provided, having the formula: CYS-$X_2$-$X_3$-$X_4$-$X_5$-$X_6$-$X_7$-$X_8$-Cys (SEQ ID NO: 2), wherein $X_2$ is Pro, Arg, Asn, Asp, Gln, Gly, Phe, Ser, Thr or Tyr; preferably $X_2$ is Pro;

$X_3$ is Ala, Asn, Asp, Gln, Glu, Gly, Ile, Leu, Met, Phe, Pro, Ser, Thr, Trp, Tyr, or Val; preferably $X_3$ is Asp, Glu, Gly, Met, or Trp;

$X_4$ is Glu, Gly, Lys, Ser, or Tyr, most preferably Glu;

$X_5$ is Pro, Asp, Glu, Asn, Gln, Glu, Gly, Leu, Lys, Ser, Thr, or Tyr; preferably, $X_8$ is Asn, Asp, Glu, Pro, or Ser; most preferably, $X_5$ is Pro;

$X_6$ is Arg, Gly, or Trp, preferably Trp;

$X_7$ is Leu, Ile, Lys, Met, Asn, Gln, Pro, Ser, Thr, or Val; preferably $X_7$ is Leu or Thr; and $X_8$ is Ile, Leu, Phe, Trp, or Tyr.

Formation of the disulfide binding loop is advantageous because it leads to increased affinity and specificity for such peptides. However, in serum, the dissulfide bond might be opened by free cysteines or other thiol-containing molecules. Thus, it may be useful to modify the amino acids at positions 4 and/or 12 to replace the disulfide cross-link with another less reactive linkage. The 15-mer peptides described above have the alpha carbons of amino acids 4 and 12 linked by a —$CH_2$—S—S—$CH_2$— cross-link comprising five covalent bonds. Typical C—C single bonds are about 1.5 Å in length, while S—S bonds are about 2.0 Å and C—S bonds are about 1.8 Å. The —$CH_2$—S—S—$CH_2$— cross-link has a preferred geometry in which the dihedral bond between sulphurs is close to 90 degrees, but the exact geometry is determined by the context of other side groups and the binding state of the molecule. Preferred modifications of the closing cross-link of the binding loop will preserve the overall bond lengths and angles as much as possible. Suitable such alternative cross-links include thioether linkages such as —$CH_2$—S—$CH_2$—$CH_2$—, —$CH_2$—$CH_2$—S—$CH_2$—, —$CH_2$—$CH_2$—S—$CH_2$—$CH_2$—; lactam linkagens such as —$CH_2$—NH—CO—$CH_2$— and —$CH_2$—CO—NH—$CH_2$—; ether linkages such as —$CH_2$—$CH_2$—O—$CH_2$—$CH_2$—; alkylene bridges such as —$(CH_2)_n$— (where n=4, 5, or 6); the linkage —$CH_2$—NH—CO—NH—$CH_2$—, and similar groups known in the art.

Although polypeptides containing a stable disulfide-linked binding loop are most preferred, linear polypeptides derived from the foregoing sequences may be readily prepared, e.g., by substitution of one or both cysteine residues, which may retain at least some of the fibrin binding activity of the original polypeptide containing the disulfide loop. In making such substitutions for Cys, the amino acids Gly, Ser, and Ala are preferred, and it is also preferred to substitute both Cys residues, so as not to leave a single Cys that may cause the polypeptide to dimerize or react with other free thiol groups in a solution. All such linearized derivatives that retain fibrin binding properties are within the scope of this invention.

Direct synthesis of the peptides of the invention may be accomplished using conventional techniques, including solid-phase peptide synthesis, solution-phase synthesis, etc. Solid-phase synthesis is preferred. See Stewart et al., *Solid-Phase Peptide Synthesis* (1989), W. H. Freeman Co., San Francisco; Merrifield, *J. Am. Chem. Soc.*, 85:2149–2154 (1963); Bodanszky and Bodanszky, *The Practice of Peptide Synthesis* (Springer-Verlag, New York 1984), incorporated herein by reference.

Polypeptides according to the invention may also be prepared commercially by companies providing peptide synthesis as a service (e.g., BACHEM Bioscience, Inc., King of Prussia, Pa.; Quality Controlled Biochemicals, Inc., Hopkinton, Mass.).

Automated peptide synthesis machines, such as manufactured by Perkin-Elmer Applied Biosystems, also are available.

The polypeptide compound is preferably purified once it has been isolated or synthesized by either chemical or recombinant techniques. For purification purposes, there are many standard methods that may be employed including reversed-phase high-pressure liquid chromatography (RP-HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptides based on their charge. The degree of purity of the polypeptide may be determined by various methods, including identification of a major large peak on HPLC. A polypeptide that produces a single peak that is at least 95% of the input material on an HPLC column is preferred. Even more preferable is a polypeptide that produces a single peak that is at least 97%, at least 98%, at least 99% or even 99.5% of the input material on an HPLC column.

In order to ensure that the peptide obtained using any of the techniques described above is the desired peptide for use in compositions of the present invention, analysis of the peptide composition may be carried out. Such composition analysis may be conducted using high resolution mass spectrometry to determine the molecular weight of the peptide. Alternatively, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

The fibrin binding polypeptides of the invention may be conformationally restrained by disulfide linkages between the two cysteine residues in their sequence. This conformational restraint ensures that the peptides have a binding structure that contributes to the peptides' affinity for fibrin and their specificity for fibrin over fibrinogen. Other methods for constraining peptides which would retain a similar conformation and fibrin specificity for the peptide have been described in the art and may be used herein, including the substitution of one or more of the cysteine residues with non-naturally occurring amino acids or peptidomimetics for the purpose of forming a more stable or conformationally preferred linkage between the two positions on the peptide. All such modified fibrin binding moieties are also considered fibrin binding moieties, so long as they retain the ability to bind fibrin or fibrin-derived polypeptides. Non-cyclized, or linear, versions of the peptides may also retain binding ability and specificity for fibrin and could also be employed in the present invention.

Homologues of the fibrin binding polypeptides described herein may be formed by substitution, addition or deletion of one or more amino acids employing methods well known in the art and for particular purposes known in the art. Such homologous polypeptides will be understood to fall within the scope of the present invention so long as the substitution, addition or deletion of amino acids does not eliminate its ability to bind fibrin. The term "homologous", as used herein, refers to the degree of sequence similarity between two polymers (i.e., polypeptide molecules or nucleic acid molecules). When the same nucleotide or amino acid residue occupies a sequence position in the two polymers under comparison, then the polymers are homologous at that position. For example, if the amino acid residues at 60 of 100 amino acid positions in two polypeptide sequences match or are homologous then the two sequences are 60% homologous. The homology percentage figures referred to herein reflect the maximal homology possible between the two polymers, i.e., the percent homology when the two polymers are so aligned as to have the greatest number of matched (homologous) positions. Polypeptide homologues within the scope of the present invention will be at least 80% and preferably greater than 90% homologous to at least one of the fibrin binding sequences disclosed herein.

Fibrin binding polypeptides according to the present invention also may be produced using recombinant DNA techniques, utilizing nucleic acids (polynucleotides) encoding the polypeptides according to this invention and then expressing them recombinantly, i.e., by manipulating host cells by introduction of exogenous nucleic acid molecules in known ways to cause such host cells to produce the desired fibrin binding polypeptides. Such procedures are within the capability of those skilled in the art (see Davis et al., *Basic Methods in Molecular Biology*, (1986)). Recombinant production of short peptides such as those described herein may not be practical in comparison to direct synthesis, however recombinant means of production may be very advantageous where a fibrin binding moiety of this invention is incorporated in a hybrid polypeptide or fusion protein.

In the practice of the present invention, a determination of the affinity of the fibrin binding moiety for fibrin relative to fibrinogen is a useful measure, and is referred to as specificity for fibrin. Standard assays for quantitating binding and determining affinity include equilibrium dialysis, equilibrium binding, gel filtration, or the monitoring of numerous spectroscopic changes (such as a change in fluorescence polarization) that may result from the interaction of the binding moiety and its target. These techniques measure the concentration of bound and free ligand as a function of ligand (or protein) concentration. The concentration of bound polypeptide ([Bound]) is related to the concentration of free polypeptide ([Free]) and the concentration of binding sites for the polypeptide, i.e., on fibrin, (N), as described in the following equation:

$$[\text{Bound}] = N \times [\text{Free}]/((1/K_a) + [\text{Free}]).$$

A solution of the data to this equation yields the association constant, $K_a$, a quantitative measure of the binding affinity. The association constant, $K_a$ is the reciprocal of the dissociation constant, $K_D$. The $K_D$ is more frequently reported in measurements of affinity. A peptide having a $K_D$ 1.5 times higher for fibrinogen than for fibrin would be considered low-specificity fibrin binder. A peptide having a $K_D$ 10 times greater for fibrinogen than fibrin would be a moderate-specificity fibrin binder, and a peptide having a $K_D$ 100 times or more greater for fibrinogen than for fibrin would be termed highly specific for fibrin. Preferably the peptides and agents of the present invention have a $K_D$ at least 1.5 times higher for fibrinogen than for fibrin, more preferably at least 10 times higher, even more preferably at least 100 times, and most preferably at least 1000 times higher. Preferred fibrin binding polypeptides have a $K_D$ for fibrin in the range of 1 nanomolar (nM) to 100 micromolar ($\mu$M) and includes $K_D$ values of at least 10 nM, at least 20 nM, at least 40 nM, at least 60 nM, at least 80 nM, at least 1 $\mu$M, at least 5 $\mu$M, at least 10 $\mu$M, at least 20 $\mu$M, at least 40 $\mu$M, at least 60 $\mu$M, and at least 80 $\mu$M.

Where fibrin binding moieties are employed as imaging agents, other aspects of binding specificity may become more important: Imaging agents operate in a dynamic system in that binding of the imaging agent to the target (a clot) is not in a stable equilibrium state throughout the imaging procedure. For example, when the imaging agent is initially injected, the concentration of imaging agent and of agent-target complex rapidly increases. Shortly after injection, however, the circulating (free) imaging agent starts to clear through the kidneys or liver, and the plasma concentration of imaging agent begins to drop. This drop in the concentration of free imaging agent in the plasma eventually causes the agent-target complex to dissociate. The usefulness of an imaging agent depends on the difference in rate of agent-target dissociation relative to the clearing rate of the agent. Ideally, the dissociation rate will be slow compared to the clearing rate, resulting in a long imaging time during which there is a high concentration of agent-target complex and a low concentration of free imaging agent (background signal) in the plasma. The dissociation rate of the complex is controlled by the dissociation rate constant, $k_{off}$. Because higher values of $k_{off}$ correspond to faster dissociation rates, it is preferable to obtain binding peptides which have a low $k_{off}$ for use as imaging agents.

To obtain peptides with a low $k_{off}$, standard display library screening procedures can be modified by replacing the standard elution step. For example, the usual procedure in library screening is to incubate the library with an immobilized target for a period sufficient to allow binders to complex with the target, then wash the immobilized complexes several times to eliminate weak and non-specific binders, then elute by changing the solution conditions around the complex to conditions that no longer support binding. Typically, elution conditions with sharply lowered pH (e.g., pH 2.0 after binding at pH 7.0) will elute many candidates for further characterization. For isolation of slow dissociating (low $k_{off}$) fibrin binders, a kinetic elution step may be substituted for the change in solution conditions. In the present case, binder-displaying phage were recovered from an immobilized fibrin target by incubating the immobilized phage/target complex with a high concentration of soluble fibrin target for long periods of time. Phage which are able to adhere to the target the longest are those which display peptides with the lowest $k_{off}$. Because only a few phage adhere to the immobilized target for extremely long time periods in the presence of excess competing ligand (i.e., soluble target), it is possible to check all of the slow-dissociating phage by ELISA. This allows the entire procedure to be performed in one round of screening, rather than the typical three to five rounds of screening necessary to observe convergence.

The fibrin binding polypeptides of the present invention are slow dissociating fibrin binders, that is, they have a low dissociation constant, as estimated by kinetic elution from an immobilized fibrin-like polypeptide target, as described below. Quantitative measurement of dissociation rates may be easily performed using several methods known in the art, such as fiber optic fluorimetry (see, e.g., Anderson & Miller, *Clin. Chem.*, 34(7):1417–21 (1988)), surface plasmon resonance (see, Malmborg et al., *J. Immunol. Methods*, 198(1):51–7 (1996) and Schuck, *Current Opinion in Biotechnology*, 8:498–502 (1997)), resonant mirror, and grating coupled planar waveguiding (see, e.g., Hutchinson, *Molec. Biotechnology*, 3:47–54 (1995)). Automated biosensors are commercially available for measuring binding kinetics: BIAcore surface plasmon resonance sensor (Biacore AB, Uppsala SE), IAsys resonant mirror sensor (Fisons Applied Sensor Technology, Cambridge GB), BIOS-1 grated coupled planar waveguiding sensor (Artificial Sensor Instruments, Zurich CH).

Uses for Fibrin Binding Polypeptides

The fibrin binding moieties according to this invention will be extremely useful for detection and/or imaging of fibrin in vitro or in vivo, and particularly for detection and/or imaging of fibrin clots. Any suitable method of assaying or imaging fibrin may be employed.

For detection of fibrin or fibrin-derived polypeptides in solution, a binding moiety according to the invention can be detectably labeled, e.g., fluorescently labeled, radiolabeled or enzymatically labeled, then contacted with the solution, and thereafter formation of a complex between the binding moiety and the fibrin target can be detected. As an example, a fluorescently labeled fibrin binding peptide may be used for in vitro fibrin detection assays, wherein the peptide is added to a solution to be tested for fibrin under conditions allowing binding to occur. The complex between the fluorescently labeled fibrin-binding peptide and fibrin can be detected and quantified by measuring the increased fluorescence polarization arising from the fibrin-bound peptide relative to that of the free peptide.

Alternatively, a sandwich-type ELISA assay may be used, wherein a fibrin binding moiety is immobilized on a solid support such as a plastic tube or well, then the solution suspected of containing fibrin or a fibrin-derived polypeptide is contacted with the immobilized binding moiety, non-binding materials are washed away, and complexed polypeptide is detected using a suitable detection reagent, such as a monoclonal antibody recognizing fibrin. The monoclonal antibody is detectable by conventional means known in the art, including being detectably labeled, e.g., radiolabeled, conjugated with an enzyme such as horseradish peroxidase and the like, or fluorescently labeled.

For detection or purification of soluble fibrin or fibrin-derived polypeptides in or from a solution, a binding moiety of the invention can be immobilized on a solid substrate such as a chromatographic support or other porous material, then the immobilized binder can be loaded or contacted with the solution under conditions suitable for formation of a binding moiety/fibrin complex. The non-binding portion of the solution can be removed and the complex may be detected, e.g., using an anti-fibrin or anti-binding moiety antibody, or the fibrin target may be released from the binding moiety at appropriate elution conditions.

The biology of fibrin and clot formation has been investigated by many researchers and continues to be an active field for research and development. Pure fibrin also may have utility as a therapeutically useful clotting agent. In furtherance of such research and development, a method of purifying bulk amounts of fibrin in pure form is desirable, and the binding moieties according to this invention are especially useful for that purpose, using the general purification methodology described above.

Thrombus Imaging

A particularly preferred use for the polypeptides according to the present invention is for creating visually readable images of thrombi, to aid in the diagnosis, monitoring and treatment of thrombus associated disorders. The fibrin binding polypeptides disclosed herein may be converted to imaging reagents for detecting thrombi by conjugating the polypeptides with a label appropriate for diagnostic detection. Preferably, a peptide exhibiting much greater specificity for fibrin than for fibrinogen is conjugated or linked to a label appropriate for the detection methodology to be employed. For example, the fibrin binder may be conjugated with a paramagnetic chelate suitable for magnetic resonance imaging (MRI), with a radiolabel suitable for x-ray imaging, with an ultrasound microsphere or liposome suitable for ultrasound detection, or with an optical imaging dye.

Suitable linkers can be substituted or unsubstituted alkyl chains, amino acid chains (e.g., polyglycine), polyethylene glycols, polyamides, and other simple polymeric linkers known in the art.

In general, the technique of using a detectably labeled fibrin binding moiety is based on the premise that the label generates a signal that is detectable outside the patient's body. When the detectably labeled fibrin binding moiety is administered to the patient suspected of having a thrombus, the high affinity of the fibrin binding moiety for fibrin in a thrombus causes the fibrin binding moiety to bind to the thrombus and accumulate label at the site of the thrombus. Sufficient time is allowed for the labeled peptide to localize at the site of the thrombus. The signal generated by the labeled peptide is detected by a scanning device which will vary according to the type of label used, and the signal is then converted to an image of the thrombus.

A. Magnetic Resonance Imaging

The fibrin binding moieties of the present invention may advantageously be conjugated with a paramagnetic metal chelate in order to form a contrast agent for use in MRI. Preferred paramagnetic metal ions have atomic numbers 21–29, 42, 44, or 57–83. This includes ions of the transition metal or lanthanide series which have one, and more preferably five or more, unpaired electrons and a magnetic moment of at least 1.7 Bohr magneton. The preferred paramagnetic metal is selected from the group consisting of Gd(III), Fe(III), Mn(II and III), Cr(III), Cu(II), Dy(III), Tb(III), Ho(III), Er(III), and Eu(III). Gd(III) is particularly preferred for MRI due to its high relaxivity and low toxicity, and the availability of only one biologically accessible oxidation state. Gd(III) chelates have been used for clinical and radiologic MR applications since 1988, and approximately 30% of MR exams currently employ a gadolinium-based contrast agent.

The practitioner will select a metal according to dose required to detect a thrombus and considering other factors such as toxicity of the metal to the subject. See, Tweedle et al., *Magnetic Resonance Imaging* (2nd ed.), vol. 1, Partain et al., eds. (W.B. Saunders Co. 1988), pp. 796–7. Generally, the desired dose for an individual metal will be proportional to its relaxivity, modified by the biodistribution, pharmacokinetics and metabolism of the metal. The trivalent cation, $Gd^{3+}$ is particularly preferred for MRI contrast agents, due to its high relaxivity and low toxicity, with the further advantage that it exists in only one biologically accessible oxidation state, which minimizes undesired metabolization of the metal by a patient. Another useful metal is $Cr^{3+}$, which is relatively inexpensive.

The organic chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclotetradecane-1,4,7,10-tetraacetic acid (DOTA), ethylenediaminetetraacetic acid (EDTA), and 1,4,8,11-tetraazacyclotetradecane-1,4,8,11-tetraacetic acid (TETA). Additional chelating ligands are ethylenebis-(2-hydroxy-phenylglycine) (EHPG), and derivatives thereof, including 5-Cl-EHPG, 5Br-EHPG, 5-Me-EHPG, 5t-Bu-EHPG, and 5sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof, the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra (methyl tetraacetic acid), and benzo-TETMA, where TETMA is 1,4,8,11-tetraazacyclotetradecane-1,4,8,11-(methyl tetraacetic acid); derivatives of 1,3-propylenediaminetetraacetic acid (PDTA) and triethylene-tetraaminehexaacetic acid (TTHA); derivatives of 1,5,10-N, N',N"-tris(2,3-dihydroxybenzoyl)-tricatecholate (LICAM) and 1,3,5-N,N',N"-tris(2,3-dihydroxybenzoyl) aminomethylbenzene (MECAM). A preferred chelator for use in the present invention is DTPA. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. No. 4,899,755, all of which are hereby incorporated by reference.

In accordance with the present invention, the chelator of the MRI contrast agent is coupled to the fibrin binding moiety. The positioning of the chelate should be selected so as not to interfere with the binding affinity or specificity of the fibrin binding moiety. Preferably, the chelate will be appended either to the N terminus or the C terminus, however the chelate may also be attached anywhere within the sequence. In preferred embodiments, a chelator having a free central carboxylic acid group (e.g., DTPA-Asp(β-COOH)—OtBu) makes it easy to attach at the N-terminus of the peptide by formation of an amide bond. The chelate could also be attached at the C-terminus with the aid of a linker. Alternatively, isothiocyanate conjugation chemistry could be employed as a way of linking the appropriate isothiocyanto group bearing DTPA to a free amino group anywhere within the peptide sequence.

In general, the fibrin binding moiety can be bound directly or covalently to the metal chelator (or other detectable label), or it may be coupled or conjugated to the metal chelator using a linker, which may be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the fibrin binding moiety); derivatized or underivatized polyethylene glycol, polyoxyethylene, or polyvinylpyridine chains; substituted or unsubstituted polyamide chains; derivatized or underivatized polyamine, polyester, polyethylenimine, polyacrylate, poly(vinyl alcohol), polyglycerol, or oligosaccharide (e.g., dextran) chains; alternating block copolymers; malonic, succinic, glutaric, adipic and pimelic acids; caproic acid; simple diamines and dialcohols; and other simple polymeric linkers known in the art (see, e.g., WO 98/18497, WO 98/18496). Preferably the molecular weight of the linker can be tightly controlled. The molecular weights can range in size from less than 100 to greater than 1000. Preferably the molecular weight of the linker is less than 100. In addition, it may be desirable to utilize a linker that is biodegradable in vivo to provide efficient routes of excretion for the imaging reagents of the present invention. Depending on their location within the linker, such biodegradable functionalities can include ester, double ester, amide, phosphoester, ether, acetal, and ketal functionalities.

In general, known methods can be used to couple the metal chelate and the fibrin binding moiety using such linkers. See, e.g., WO 95/28967, WO 98/18496, WO 98/18497 and discussion therein. The fibrin binding moiety can be linked through its N- or C-terminus via an amide bond, for example, to a metal coordinating backbone nitrogen of a metal chelate or to an acetate arm of the metal chelate itself. The present invention contemplates linking of the chelate on any position, provided the metal chelate retains the ability to bind the metal tightly in order to minimize toxicity. Similarly, the fibrin binding moiety may be modified or elongated in order to generate a locus for attachment to a metal chelate, provided such modification or elongation does not eliminate its ability to bind fibrin.

MRI contrast reagents prepared according to the disclosures herein may be used in the same manner as conventional MRI contrast reagents. When imaging a thrombus, certain MR techniques and pulse sequences may be preferred to enhance the contrast of the thrombus to the background blood and tissues. These techniques include (but are not limited to), for example, black blood angiography sequences that seek to make blood dark, such as fast spin echo sequences (see, e.g., Alexander et al., *Magnetic Resonance in Medicine*, 40(2): 298–310 (1998)) and flow-spoiled gradient echo sequences (see, e.g., Edelman et al., *Radiology*, 177(1): 45–50 (1990)). These methods also include flow independent techniques that enhance the difference in contrast due to the $T_1$ difference of contrast-enhanced thrombus and blood and tissue, such as inversion-recovery prepared or saturation-recovery prepared sequences that will increase the contrast between thrombus and background tissues. In addition, since the present invention does not significantly alter $T_2$, methods of $T_2$ preparation may also prove useful (see, e.g., Gronas et al., *Journal of Magnetic Resonance Imaging*, 7(4): 637–643 (1997)). Finally, magnetization transfer preparations may also improve contrast with these agents (see, e.g., Goodrich et al., *Investigative Radiology*, 31(6): 323–32 (1996)).

The labeled reagent is administered to the patient in the form of an injectable composition. The method of administering the MRI contrast agent is preferably parenterally, meaning intravenously, intraarterially, intrathecally, interstitially, or intracavitarilly. For imaging thrombi, intravenous or intraarterial administration is preferred. For MRI, it is contemplated that the subject will receive a dosage of contrast agent sufficient to enhance the MR signal at the site of a thrombus at least 10%. After injection with the fibrin binding moiety-containing MRI reagent, the patient is scanned in the MRI machine to determine the location of any thrombi. In therapeutic settings, upon thrombus localization, a thrombolytic can be immediately administered, if necessary, and the patient can be subsequently scanned to visualize thrombus degradation.

B. Ultrasound Imaging

When ultrasound is transmitted through a substance, the acoustic properties of the substance will depend upon the velocity of the transmissions and the density of the substance. Changes in the acoustic properties will be most prominent at the interface of different substances (solids, liquids, gases). Ultrasound contrast agents are intense sound wave reflectors because of the acoustic differences between liquid (e.g., blood) and gas-containing microbubbles, liposomes, or microspheres dissolved therein. Because of their size, ultrasound microbubbles, liposomes, microspheres, and the like may remain for a longer time in the blood stream after injection than other detectable moieties; a targeted fibrin-specific ultrasound agent therefore may demonstrate superior imaging of thrombi.

In this aspect of the invention, the fibrin binding moiety may be linked to a material which is useful for ultrasound imaging. The materials are employed to form vesicles (e.g., liposomes, microbubbles, microspheres, or emulsions) containing a liquid or gas which functions as the detectable label (e.g., an echogenic gas or material capable of generating an echogenic gas). Materials for the preparation of such vesicles include surfactants, lipids, sphingolipids, oligolipids, phospholipids, proteins, polypeptides, carbohydrates, and synthetic or natural polymeric materials. See, for further description of suitable materials and methods, WO 98/53857, WO 98/18498, WO 98/18495, WO 98/18497, WO 98/18496, and WO 98/18501.

Suitable gases include, but are not limited to, $C_{1-6}$ perfluorcarbon gases, $SF_6$, low molecular weight $C_{1-6}$ fluorinated or halogenated alkenes, alkynes, or cyclized versions of the same, or other suitable gases or mixtures thereof, as described in WO 97/29783, WO 98/53857, WO 98/18498, WO 98/18495, WO 98/18496, WO 98/18497, WO 98/18501, WO 98/05364, WO 98/17324. The term "gas" as used herein refers to materials that are in the gaseous state at the normal human body temperature of 37° C. The ultrasound vesicles may be used as is or stabilized with surfactants or some other stabilizing material such as emulsifying agents and/or viscosity enhancers, cryoprotectants, lyoprotectants, or bulking agents.

Since ultrasound vesicles may be larger than the other detectable labels described herein, they may be linked or conjugated with a plurality of fibrin binding moieties on their surfaces in order to increase the targeting efficiency of the agent. Attachment may be via direct covalent bond between the fibrin binding moiety and the material used to make the vesicle or via a linker, as described previously. For example, see WO 98/53857 generally for a description of the attachment of a peptide to a bifunctional PEG linker, which is then reacted with a liposome composition. See also, Lanza et al., *Ultrasound in Med. & Bio.*, 23(6): 863–870 (1997). The targeted ultrasound vesicles may be prepared using conventional methods known in the art. Known methods include gentle shaking, rotor mixing, sonication, high pressure homogenization, high speed stirring, high shear mixing, emulsification, and colloidal mill procedures, in the presence or absence of the desired echogenic gas or gas mixture, to generate the vesicles. The desired echogenic gas may alternatively be incorporated into the vesicles by applying an atmosphere or overpressure of said gas to the vesicles (see U.S. Pat. No. 5,674,469).

Ultrasound imaging techniques which may be used in accordance with the present invention include known techniques, such as color Doppler, power Doppler, Doppler amplitude, stimulated acoustic imaging, and two- or three-dimensional imaging techniques. Imaging may be done in harmonic (resonant frequency) or fundamental modes, with the second harmonic preferred.

C. Optical Imaging, Sonoluminescence or Photoacoustic Imaging

In accordance with the present invention, a number of optical parameters may be employed to determine the location of fibrin with in vivo light imaging after injection of the subject with an optically-labeled fibrin binding moiety. Optical parameters to be detected in the preparation of an image may include transmitted radiation, absorption, fluorescent or phosphorescent emission, light reflection, changes in absorbance amplitude or maxima, and elastically scattered radiation. For example, biological tissue is relatively translucent to light in the near infrared (NIR) wavelength range of 650–1000 nm. NIR radiation can penetrate tissue up to several centimeters, permitting the use of the fibrin binding moieties of the present invention for optical imaging of fibrin in vivo.

The fibrin binding moieties may be conjugated with photolabels, such as optical dyes, including organic chromophores or fluorophores, having extensive delocalized ring systems and having absorption or emission maxima in the range of 400–1500 nm. The fibrin binding moiety may alternatively be derivatized with a bioluminescent molecule. The preferred range of absorption maxima for photolabels is between 600 and 1000 nm to minimize interference with the signal from hemoglobin. Preferably, photoabsorption labels have large molar absorptivities, e.g. $>10^5$ cm$^{-1}$M$^{-1}$, while fluorescent optical dyes will have high quantum yields. Examples of optical dyes include, but are not limited to those described in WO 98/18497, WO 98/18496, WO 98/18495, WO 98/18498, WO 98/53857, WO 96/17628, WO 97/18841, WO 96/23524, WO 98/47538, and references cited therein. The photolabels may be covalently linked directly to the fibrin binding moiety or linked to the fibrin binding moiety via a linker, as described previously.

After injection of the optically-labeled fibrin binding moiety, the patient is scanned with one or more light sources (e.g., a laser) in the wavelength range appropriate for the photolabel employed in the agent. The light used may be monochromatic or polychromatic and continuous or pulsed. Transmitted, scattered, or reflected light is detected via a photodetector tuned to one or multiple wavelengths to determine the location of fibrin in the subject. Changes in the optical parameter may be monitored over time to detect accumulation of the optically-labeled reagent at the site of the thrombus. Standard image processing and detecting devices may be used in conjunction with the optical imaging reagents of the present invention.

The optical imaging reagents described above may also be used for acousto-optical or sonoluminescent imaging performed with optically-labeled imaging agents (see, U.S. Pat. No. 5,171,298, WO 98/57666, and references therein). In acousto-optical imaging, ultrasound radiation is applied to the subject and affects the optical parameters of the transmitted, emitted, or reflected light. In sonoluminescent imaging, the applied ultrasound actually generates the light detected. Suitable imaging methods using such techniques are described in WO 98/57666.

D. Nuclear Imaging (Radionuclide Imaging).

The fibrin binding moieties may be conjugated with a radionuclide reporter appropriate for scintigraphy, SPECT, or PET imaging. For use as a PET agent a peptide is complexed with one of the various positron emitting metal ions, such as $^{51}$Mn, $^{52}$Fe, $^{60}$Cu, $^{68}$Ga, $^{72}$As, $^{94m}$Tc, or $^{110}$In. Preferred metal radionuclides include $^{90}$Y, $^{99m}$Tc, 111In, $^{47}$Sc, $^{67}$Ga, $^{51}$Cr, $^{177m}$Sn, $^{67}$Cu, $^{167}$Tm, $^{97}$Ru, $^{188}$Re, $^{177}$Lu, $^{199}$Au, $^{203}$Pb, and $^{141}$Ce. $^{99m}$Tc is preferred because of its low cost, availability, imaging properties, and high specific activity. The nuclear and radioactive properties of Tc-99m make this isotope an ideal scintigraphic imaging agent. This isotope has a single photon energy of 140 keV and a radioactive half-life of about 6 hours, and is readily available from a $^{99}$Mo-$^{99m}$Tc generator. The radioactive metals may be chelated by, for example, linear, macrocyclic, terpyridine, and $N_3S$, $N_2S_2$, or $N_4$ chelants (see also, U.S. Pat. Nos. 5,367,080, 5,364,613, 5,021,556, 5,075,099, 5,886,142), and other chelators known in the art including, but not limited to, HYNIC, DTPA, EDTA, DOTA, TETA, and bisamino bisthiol (BAT) chelators (see also U.S. Pat. No. 5,720,934). The chelates may be covalently linked directly to the fibrin binding moiety or linked to the fibrin binding moiety via a linker, as described previously, and then directly labeled with the radioactive metal of choice (see, WO 98/52618, U.S. Pat. Nos. 5,879,658, and 5,849,261).

In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a peptide of this invention conjugated with an appropriate chelator with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

Generally, the unit dose to be administered has a radioactivity of about 0.01 mCi to about 100 mCi, preferably 1 mCi to 20 mCi. The solution to be injected at unit dosage is from about 0.01 mL to about 10 mL.

Typical doses of a radionuclide-labeled fibrin binding imaging agents according to the invention provide 10–20 mCi. After injection of the fibrin-specific radionuclide imaging agent into the patient, a gamma camera calibrated for the gamma ray energy of the nuclide incorporated in the imaging agent is used to image areas of uptake of the agent and quantify the amount of radioactivity present in the clot. Imaging of the thrombus in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

Therapeutic Applications

The fibrin binding polypeptides of the present invention can be used to improve the activity of thrombolytic agents against clots by providing or improving their affinity for fibrin and their residence time at a fibrin clot. In this aspect of the invention, hybrid thrombolytic agents are provided by conjugating a fibrin binding polypeptide according to the invention with a thrombolytic agent. The fibrin binding polypeptide portion of the conjugate causes the thrombolytic to "home" to the sites of fibrin clots, and to improve the affinity of the conjugate for the clots, so that the thrombolytic activity of the conjugate is more localized and concentrated at the sites of clots. Such conjugates will be useful in treating thrombus associated diseases, especially acute myocardial infarction, in mammals, including humans, which method comprises administering to a mammal in need thereof an effective amount of a fibrin binding moiety according to the invention conjugated with a thrombolytic agent. The invention also provides the use of such conjugates in the manufacture of a medicament for the treatment of thrombus associated diseases in mammals, including humans. Suitable thrombolytic agents for use in this aspect of the invention include fibrinolytic enzymes, including plasminogen activators. The term plasminogen activator includes but is not limited to streptokinase, human tissue plasminogen activator (tPA) and urokinase (both single and two-chain forms). Such enzymes are obtained from natural sources or tissues or by recombinant production. Other suitable thrombolytic agents include fibrinolytically active hybrid proteins (see, e.g., EP-A-155 387) which comprise one chain of a 2-chain protease linked to a chain of a different 2-chain protease, at least one of the chains in the hybrid protein being derived from a fibrinolytically active protease; thrombolytic protein conjugates (see, e.g., EP-A-152 736), such as urokinase linked to reversibly blocked plasmin; derivatives of fibrinolytic enzymes in which the catalytic site on the enzyme which is responsible for fibrinolytic activity is blocked by a human protein attached thereto by way of a reversible linking group, for example urokinase reversibly linked to the active center of human plasmin; genetically engineered derivatives including muteins of naturally occurring plasminogen activators; hybrid molecules (see, e.g., EP-A-297 882); reversibly blocked in vivo fibrinolytic enzymes, such as a binary complex between streptokinase and plasminogen, most preferably a p-anisoyl streptokinase/plasminogen complex without internal bond cleavage (anistreplase, described in U.S. Pat. No. 4,808,405); and the like.

The thrombolytic agents and the fibrin binding moieties can be linked or fused in known ways, using the same type of linkers discussed above with respect to constructing MRI contrast agents. Preferred linkers will be substituted or unsubstituted alkyl chains, amino acid chains, polyethylene glycol chains, and other simple polymeric linkers known in the art. More preferably, if the thrombolytic agent is itself a protein, for which the encoding DNA sequence is known, the thrombolytic protein and fibrin binding polypeptide may be coexpressed from the same synthetic gene, created using recombinant DNA techniques, as described above. The coding sequence for the fibrin binding polypeptide may be fused in frame with that of the thrombolytic protein, such that the peptide is expressed at the amino- or carboxy-terminus of the thrombolytic protein, or at a place between the termini, if it is determined that such placement would not destroy the required biological function of either the thrombolytic protein or fibrin binding polypeptide. A particular advantage of this general approach is that concatamerization of multiple, tandemly arranged fibrin binding polypeptides is possible, thereby increasing the number and concentration of fibrin binding sites associated with each thrombolytic protein. In this manner fibrin binding avidity is increased which would be expected to improve the efficacy of the recombinant therapeutic protein.

In addition to thrombolytic agents, the fibrin binding peptides according to this invention can be used to deliver other active agents to sites of fibrin in vivo or in vitro. For example, small molecule therapeutics or other therapeutic agents may be linked to one or more fibrin binding peptides and the conjugate administered to a subject or introduced to a fibrin-containing solution, and the fibrin-binding properties of the conjugate will concentrate the small molecule or therapeutic agent at the sites of fibrin accumulation. In a particularly preferred aspect, the fibrin binding peptides of the invention may be used to deliver agents which are active in the presence of fibrin, such as angiogenesis promoters (e.g., fibroblast growth factor). The fibrin binding peptides may also be used to increase the blood clearance half-life of a compound or drug, by causing accumulation of the compound or drug in fibrin clots, from which it will be gradually released.

In the above treatment methods, the compounds may be administered by any convenient route customary for thrombolytic agents, for example by infusion or bolus injection. In a preferred embodiment, the composition may be formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anaesthetic such as lignocaine to ease pain at the site of the injection. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline may be provided so that the ingredients may be mixed prior to administration.

The quantity of material administered will depend on the seriousness of the thromboembolic condition and position and size of the clot. The precise dose to be employed and mode of administration must per force in view of the nature of the complaint be decided according to the circumstances by the physician supervising treatment. In general, dosages of the fibrin binder/thrombolytic agent conjugate will follow the dosages that are routine for the thrombolytic agent alone, although the improved affinity for fibrin added by the fibrin binder component may allow a decrease in the standard thrombolytic dosage. Particular thrombolytics contemplated for use in this therapy (with examples of dose and method of administration) are as follows:

| | |
|---|---|
| streptokinase | 1.0–3.0 megaunits over 30 minutes to 3 hours |
| anistreplase | 30 units; 2–5 minute injection |
| tPA (wild-type) | 50–150 mg; infusion over up to 6 hours |
| two-chain urokinase | 40–100 mg; infusion over up to 6 hours |
| single-chain urokinase | (3–12 megaunits) 30–100 mg; infusion over up to 5 hours |
| hybrid plasminogen activators and derivatives | 20–100 mg; injection or infusion |
| muteins of plasminogen activators | 10–100 mg; injection or infusion |

In preferred features, the fibrin binding moiety is linked to the thrombolytic agent with a linker encompassing an enzymatic cleavage site, e.g., an enzymatic cleavage site normally cleaved by enzymes in the coagulation cascade, such as Factor Xa, thrombin, or plasmin cleavage sites, etc. The thrombolytic agent preferably would not be activated until it is cleaved from the fibrin binding moiety at the site of the clot. Since cleavage of the thrombolytic agent would occur at the site of the clot, the risk of unwanted bleeding events at sites distant from the clot would be minimized.

Alternatively, a therapeutic thrombolytic can be loaded into an ultrasound vesicle that has been derivatized on its surface with the fibrin binding moieties of the present invention. The vesicle may also be filled with an ultrasound efficient gas, such as, but not limited to, perfluoropropane or perfluorobutane. Once the fibrin-specific vesicle has homed to the site of a thrombus, as monitored by ultrasound, the frequency and energy of the ultrasound waves administered can be altered to result in a controlled release of the thrombolytic at the site of the thrombus (see, e.g., WO 93/25241).

Pharmaceutical Applications

Whether the fibrin binding moieties are to be used in patients for detection and diagnosis or to facilitate the therapeutic degradation of thrombi, such uses require that they be treated as pharmaceutical agents. Pharmaceutical compositions of this invention comprise any of the compounds of the present invention, and pharmaceutically acceptable salts thereof, with any pharmaceutically acceptable ingredient, excipient, carrier, adjuvant or vehicle.

Pharmaceutical compositions of this invention can be administered to mammals including humans in a manner similar to other diagnostic or therapeutic agents. The dosage to be administered, and the mode of administration will depend on a variety of factors including age, weight, sex, condition of the patient, and genetic factors, and will ultimately be decided by the attending physician or veterinarian. In general, dosage required for diagnostic sensitivity or therapeutic efficacy will range from about 0.001 to 50,000 $\mu$g/kg, more usually 0.01 to 25.0 $\mu$g/kg of host body mass.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered by a variety of routes or modes. These include, but not limited, to oral, intratracheal, sublingual, pulmonary, topical, rectal, nasal, buccal, vaginal, parenteral, or via an implanted reservoir. Implanted reservoirs may function by mechanical, osmotic, or other means. The term parenteral as used herein includes intraperitoneal, paravertebral, periarticular, periostal, subcutaneous, intracutaneous, intravenous, intra-arterial, intramuscular, intra-articular, intrasynovial, intrasternal, intrathecal, intralesional and intracranial injection or infusion techniques.

Such compositions are preferably formulated for parenteral administration, and most preferably for intravenous or intra-arterial administration. Generally, and particularly when administration is intravenous or intra-arterial, pharmaceutical compositions may be given as a bolus, as two or more doses separated in time, or as a constant or non-linear flow infusion.

Details concerning dosages, dosage forms, modes of administration, composition and the like are further discussed in a standard pharmaceutical text, such as *Remington's Pharmaceutical Sciences*, 18th ed., Alfonso R. Gennaro, ed. (Mack Publishing Co., Easton, Pa. 1990), which is hereby incorporated by reference.

Use of Fibrin Binding Polypeptides to Screen Molecular Libraries

Complexes formed between fibrin and fibrin binding moieties of the present invention may also be used to screen small molecule libraries to discover non-peptidergic, peptidomimetic, or other molecular entities or compounds capable of binding specifically and with high affinity to fibrin. Such novel fibrin binding compounds, which may bind fibrin reversibly or covalently, may find uses comparable to or different than those currently envisioned for the fibrin binding moieties of the present invention.

Screening is preferably performed in a high-throughput format. In one version of the screen, fibrin binding polypeptides as described herein are detectably labeled and added in solution to fibrin protein attached to a surface, including, but not limited to, wells of a plastic assay plate (e.g., polystryrene 96-well plates), and allowed to form noncovalent complexes. Fibrin/binding polypeptide binding may or may not be allowed to reach equilibrium. Subsequently, a single concentration of unlabeled test compound is added to one well, or multiple concentrations of a test compound is added to multiple wells, and time allowed to enable partial or full equilibrium among fibrin, labeled polypeptide and test compound. If the test compound binds fibrin, then some labeled peptide will be competitively displaced, in proportion to the binding affinity between the test compound and fibrin. The well is washed to remove non-fibrin bound labeled peptide and test compound, after which residual non-displaced labeled peptide is detected, such as by an ELISA plate reader. Test compounds capable of displacing a threshold amount of labeled peptide, as adjudged by comparison to appropriate positive and negative controls, are identified as putative fibrin binding molecular entities which are further studied with regard to their physical, chemical, biological, and pharmacological properties.

In an alternative embodiment of the high-throughput assay, the labeled polypeptide is mixed with the test compound, each of which is simultaneously added to the well containing the bound fibrin protein. In yet another embodiment, the fibrin binding polypeptide is attached to the solid surface, and the fibrin is detectably labeled.

Comparison between the effectiveness with which a concentration range of test compound and an unlabeled version of a fibrin binding polypeptide of known affinity displaces a given concentration of labeled peptide of the same species provides an estimate of the fibrin binding affinity of the test compound.

Isolation of fibrin binding moieties in accordance with this invention will be further illustrated in the following examples. The specific parameters included in the following examples are intended to illustrate the practice of the invention, and they are not presented to in any way limit the scope of the invention.

EXAMPLE 1
Preparation of a Fibrin Target for Library Screening

For screening libraries to isolate binding moieties for fibrin, the soluble fibrin-derived polypeptide DD(E) was prepared following a modification of a published method (Moskoitz and Budzynksi, *Biochemistry,* 33: 12937–12944 (1994) and references therein). Fibrinogen containing a Factor XIII trace impurity (1 g, Grade L; purchased from American Diagnostica) was dissolved in TBS buffer and dialyzed overnight against TBS containing 5 mM citrate. The fibrinogen concentration was adjusted to 3.0 mg/ml and $CaCl_2$ was added to a concentration of 10 mM. Clotting of the fibrinogen was initiated by the addition of thrombin to 0.5 U/ml and the clot was incubated for 3 hours at 37° C. The clot was cut up with a spatula to release water and to concentrate the clot. The clot pieces were washed twice with TBS.Ca buffer (TBS containing 2 mM $CaCl_2$) and were centrifuged at 4,000×g to compact the clots between washes. The clot material was resuspended in 250 ml TBS containing 25 mM $CaCl_2$ and 2 K.I.U. plasmin per mg fibrin. The clots were digested overnight at 20° C. Undigested clot was removed by pipette, and the supernatant was shaken with 10 ml of Lysine Sepharose (Pharmacia) for 30 minutes and filtered to remove the resin. Aprotinin was added to the filtrate to a concentration of 500 U/$\mu$L. Ammonium sulfate was added to 30% saturation and the precipitated protein was removed by centrifugation. More ammonium sulfate was added to the supernatant to a final concentration of 50% saturation, and the precipitated protein was concentrated by centrifugation. The pellets, containing DD(E), were resuspended in a small volume of buffer (50 mM Tris, 150 mM NaCl, 2 mM $CaCl_2$) (<10 ml) and chromatographed on a SEPHACRYL S200 (Pharmacia) size exclusion column (5×100 cm) in the same buffer. Fractions of protein eluted from the column were assayed by SDS-PAGE for DD(E). DD(E) contains subunits of 55 kD (Fragment E) and 190 kD (Fragment DD).

To prepare the DD(E) as a target for library screening, the complex was first biotinylated. The buffer was changed to 50 mM sodium phosphate and reacted with 10 equivalents of sulfo-NHS-LC-biotin (Pierce Chemical Co.), an aminofunctional compound that adds biotin moiety to aminereactive sites. Magnetic beads (Dynal, Inc.), coated with the biotin-binding protein streptavidin, were then coated with the biotinylated DD(E). Roughly 100 pmol of DD(E) were immobilized per milligram of beads. The beads were then suspended in 100 $\mu$L of buffer containing 50 mM Tris, 150 mM NaCl, 2 mM $CaCl_2$, 0.05% Tween-20, and 0.1% human serum albumin to block sites against nonspecific binding.

EXAMPLE 2
Screening of Phage Display Libraries

Several phage display libraries, including a TN6/VI phage library displaying variegated exogenous single-loop peptides based on a polypeptide template having the structure Xaa-Xaa-Xaa-Cys-Xaa-Xaa-Xaa-Xaa-Cys-Xaa-Xaa-Xaa (SEQ ID NO: 13) ($3.3 \times 10^{12}$ peptide diversity displayed on M13 phage) was diluted into 100 $\mu$L of binding buffer (50 mM Tris, 150 mM NaCl, 2 mM $CaCl_2$, 0.05% Tween-20).

Before selecting phage that bound to the fibrin or DD(E) targets, at the beginning of each screening round, the libraries were depleted of fibrinogen binders: Fibrinogen was biotinylated by the same method employed for DD(E) biotinylation, and then immobilized on magnetic beads. The beads were aliquoted into five tubes. The phage library was incubated with the beads in the first tube for 10 minutes, the beads were pelleted with a magnet, and the supernatant, now at least partially depleted of fibrinogen binding phage, was transferred to a second tube. This process was repeated over the five tubes, and after the last depletion, the library was introduced to the microtiter plates containing the immobilized DD(E) target, prepared as above. After a 2-hour incubation with the target to allow binding of phage to DD(E), the wells of the plate were washed extensively (15 times) to remove unbound or weakly bound phage. Bound phage were recovered by eluting the phage from the target in pH 2.0 citrate buffer (10 mM citrate, 150 mM NaCl). The recovered phage were propagated and prepared for use in the succeeding round of selection. In all, five rounds of depletion and selection were conducted. After each round, the phage eluted were counted to determine if the amount of phage recovered (as a percent of the input) increased, an indication that the screening process was converging on a small family of sequences.

EXAMPLE 3
Analysis of High $k_{off}$ Isolates

After five rounds of selection, the eluted phage were propagated and a portion plated to isolate phage plaques arising from individual clones. Ninety such clones were selected randomly, propagated, and tested individually for binding to fibrin in a dried fibrin plate assay. Dried fibrin plates were prepared as described above for the library screening. Phage samples (~$10^9$ phage each) were incubated in the dried fibrin plate wells in binding buffer (50 mM Tris, 150 mM NaCl, 2 mM $CaCl_2$, 0.05% Tween-20) containing 0.1% HSA. After 1 hour, the plates were washed 5 times with binding buffer. Anti-M13 antibody conjugated to horseradish peroxidase (Pharmacia) was added at 1/5000 dilution in binding buffer to the wells and incubated with the fibrin for 1 hour. The wells were again washed 5 times with binding buffer and the presence of the antibody/phage/fibrin complex was measured with HRP calorimetric reagents (3,3',5,5'-tetramethylbenzidine (TMB) and $H_2O_2$). A high absorbance at 595 nm (due to oxidized TMB) was indicative of a tight phage/fibrin interaction, and phage clones corresponding to those wells were identified as bearing fibrin-binding moieties.

These fibrin-binding positive clones were subjected to several secondary ELISA assays. These assays followed a similar protocol to that detailed above for the dried fibrin ELISA assay, the only variations being the method of target immobilization and the omission of HSA from binding and wash buffers. A screen against DD(E) acted as a further confirmation of fibrin binding activity. An ELISA screen against fibrinogen (immobilized to the plate by the biotin/streptavidin protocol used for DD(E)) was a check against fibrinogen binding and confirmed that the negative selection procedure detailed in Example 2 had been effective. Finally, ELISAs to assay binding to immobilized HSA (passively bound to the polystyrene plate) and a target-free microtiter plate were controls to eliminate phage that bound promiscuously or nonspecifically.

The amino acid sequences of the phage-displayed polypeptides from the ELISA positive clones (those positive for fibrin, but negative for fibrinogen, HSA and the polystyrene plate) were deduced by DNA sequencing. The high affinity fibrin binding polypeptides isolated in this manner are described in WO 01/09188, which is incorporated herein by reference. Dissociation constants with respect to fibrin were determined for many of the fibrin binders isolated as described above, using the following method:

A fibrinogen solution was prepared at 10 mg/ml (or at twice the concentration of fibrin desired) in TBS buffer (50 mM Tris, 150 mM NaCl, pH 7.4). The fibrinogen solution typically contained ~17 mM citrate. Subsequently, a solution was prepared containing 2 U/ml thrombin, 20 mM $CaCl_2$, and 5 mM ε-aminocaproic acid in TBS. The fibrinogen solution and thrombin solution were mixed 1:1 in the wells of a 96-well plate, aliquoting 50 μL of each solution in each well (total volume=100 μL). The plates were evaporated to dryness overnight at 37° C. The polypeptide to be tested, dissolved in water, was added to each well at concentrations between 1–200 μM. A typical binding assay contained 24 points at concentrations of 2, 4, 6, 8, 10, 12, 14, 17, 20, 23, 26, 30, 35, 40, 45, 50, 60, 70, 80, 100, 125, 150, 175, and 200 μM. The plate containing the peptide and (rehydrated) dried fibrin was covered and incubated at 37° C. on a shaker table for 2 hours.

The supernatant in each well was removed by pipette and the concentration of the polypeptide was measured by mass spectrometry. The ion current detected at the mass of the peptide was monitored after injection of a sample into the mass spectrometer. The area-under-the-peak was quantified and compared to standards of known concentration. The concentration of peptide in the supernatant is equal to the concentration of free peptide. The concentration of bound peptide was determined by subtracting the concentration of free peptide from the total (starting) concentration. A plot of [Bound Peptide] vs. [Free Peptide] was used to determine the $K_d$ and the concentration of bound peptide at saturation. The curve was fit to the equation:

$$[Bound]=N\times[Free]/(K_d+[Free])$$

where [Bound] is the concentration of bound polypeptide, [Free] is the concentration of free polypeptide, $K_d$ is the dissociation constant (equal to the reciprocal of $K_a$) and N is the concentration of binding sites. The number of binding sites per fibrin molecule was equal to the concentration of binding sites determined by the [Bound Polypeptide] vs. [Free Polypeptide] plot, divided by the concentration of fibrin (15 μM) used in the assay.

The dissociation constants for synthetic fibrin binding polypeptides isolated as set forth above ranged from about 700 nM to about 13 μM and above. After working with various embodiments, the synthetic peptide DX-101, having the sequence: Ala-Glu-Gly-Thr-Gly-Ser-Gln-Trp-Glu-Cys-Pro-Tyr-Gly-Leu-Cys-Trp-Ile-Gln-Ala-Pro-Gly-Lys (SEQ ID NO: 14) showed the lowest $K_D$ (700 nM) with respect to fibrin.

Additionally, the dissociation constants ($K_D$) between the peptides and DD(E) were measured using fluorescence polarization and fluorescein-labeled versions of the peptides (see Lakowicz, *Principles of Fluorescence Spectroscopy* (1983), Plenum Press, New York). The $K_D$ values thus obtained are similar to those observed for fibrin as described above.

Further screening to obtain high affinity fibrin binding polypeptides having even lower $K_D$ and having a lower rate of dissociation from fibrin targets was performed.

EXAMPLE 4
Kinetic Elution of Low $k_{off}$ Fibrin Binders

To obtain peptides with a low $k_{off}$, the normal screening procedure was modified by replacing the standard elution step in the procedure described in Example 2. In this case, phage were eluted from the immobilized DD(E) target by incubating the immobilized phage/DD(E) target complexes in binding buffer with a high concentration of soluble DD(E) for long periods of time.

Phage libraries TN7/IV, TN8/IX, and TN9/IV, which had been depleted of fibrinogen binders using the same technique described above were incubated as described above with immobilized DDE to capture fibrin binders, washed to eliminate non-binding phage, and subsequently eluted with serial applications of 300 μL volumes of 0.1 mg/mL DD(E). The number of phage in each volume of eluate was analyzed by phage titering. As hoped, the rate at which phage were released from the immobilized target decreased with longer elution time. (See FIG. 1)

Individual phage isolates were recovered from the elutions of longest duration and screened by ELISA to detect specific binders of DD(E) which do not bind fibrinogen. The ELISAs were performed as described above. The isolates with the desired binding selectivity were sequenced, and the resulting sequences are shown in Table 1.

TABLE 1

Sequences of Low $k_{off}$ Isolates Which Selectively Bind Fibrin

| Phage Isolate | Sequence | Library | SEQ ID NO: |
|---|---|---|---|
| 002-35-E01 | WELCSDENWLWCWPH | TN9/IV | 3 |
| 002-36-A02 | WMMCPMSEWLYCWSA | TN9/IV | 4 |
| 002-37-C11 | WQPCPWESWTFCWDP | TN9/IV | 5 |
| 002-37-D02 | WAPCQEEPWLFCFHG | TN9/IV | 6 |
| 002-37-H02 | WKACPGEDWLFCWGS | TN9/IV | 7 |
| 002-36-H04 | RAPCDYYGTCVEL | TN7/IV | 8 |

Two of the slow-dissociating fibrin binding sequences, 002-37-C11 and 002-37-D02 were used to design synthetic peptides that were examined in further experiments. Synthetic peptide structures are shown in Table 2. All peptides were N-terminally acylated (Ac), and C-terminally amidated (—C:O—NH$_2$) to aid in immobilization.

TABLE 2

Synthetic peptides based on 002-37-C11 and 002-37-D02 fibrin binders

| Peptide | Structure | SEQ ID NO: |
|---|---|---|
| DX-287 | Ac-WQPCPWESWTFCWDPGGGK-NH$_2$ | 15 |
| DX-328 | Ac-WQPCPWESWTFCWDPGGGK(HYNIC)-NH$_2$ | 16 |
| DX-303 | Ac-WQPCPWESWTFCWDPGGGK(fluorescein)-NH$_2$ | 7 |
| DX-288 | Ac-WAPCQEEPWLFCFHGGGGK-NH$_2$ | 18 |
| DX-329 | Ac-WAPCQEEPWLFCFHGGGGK(HYNIMC)-NH$_2$ | 19 |
| DX-304 | Ac-WAPCQEEPWLFCFHGGGGK(fluorescein)-NH$_2$ | 20 |

Figure 2:
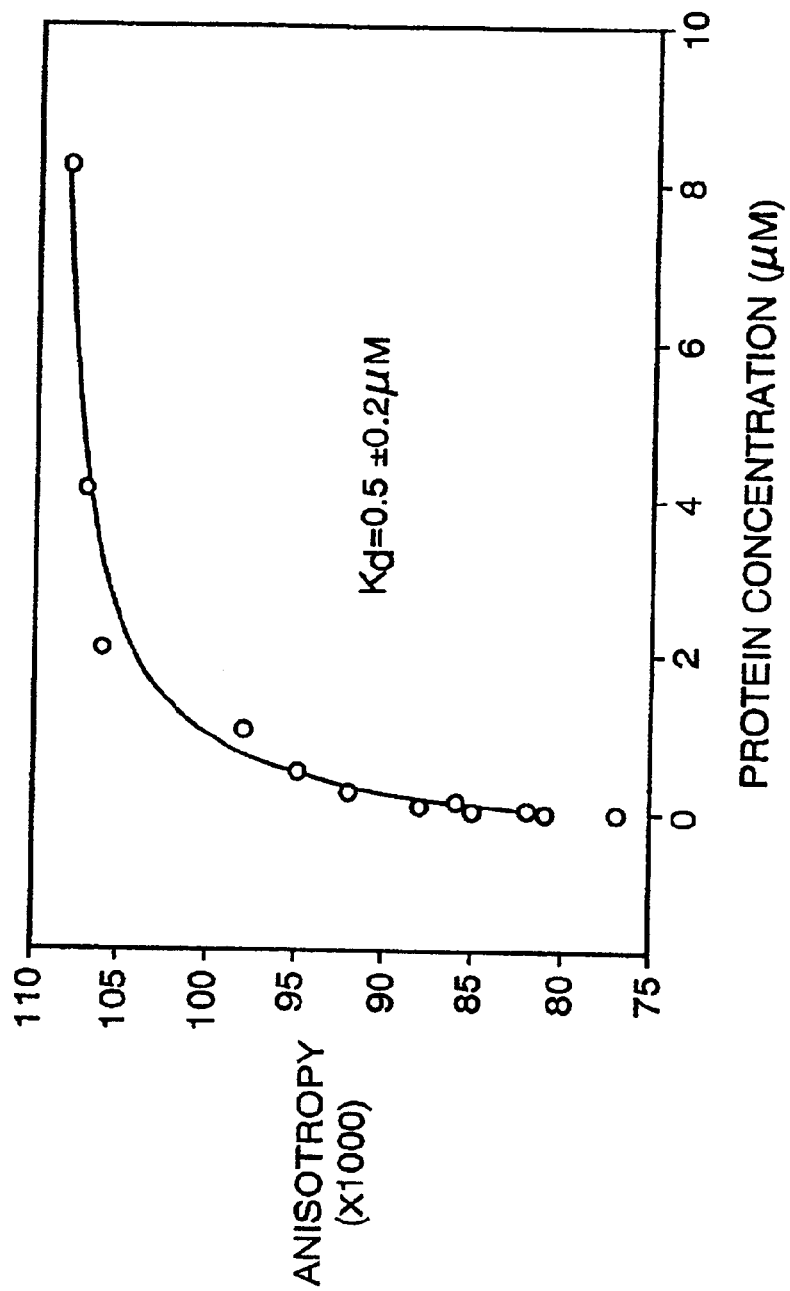
FIG. 2 illustrates the determination of the dissociation constant for synthetic fibrin-binding peptide DX-303 by fluorescence anisotropy.
Figure 3:
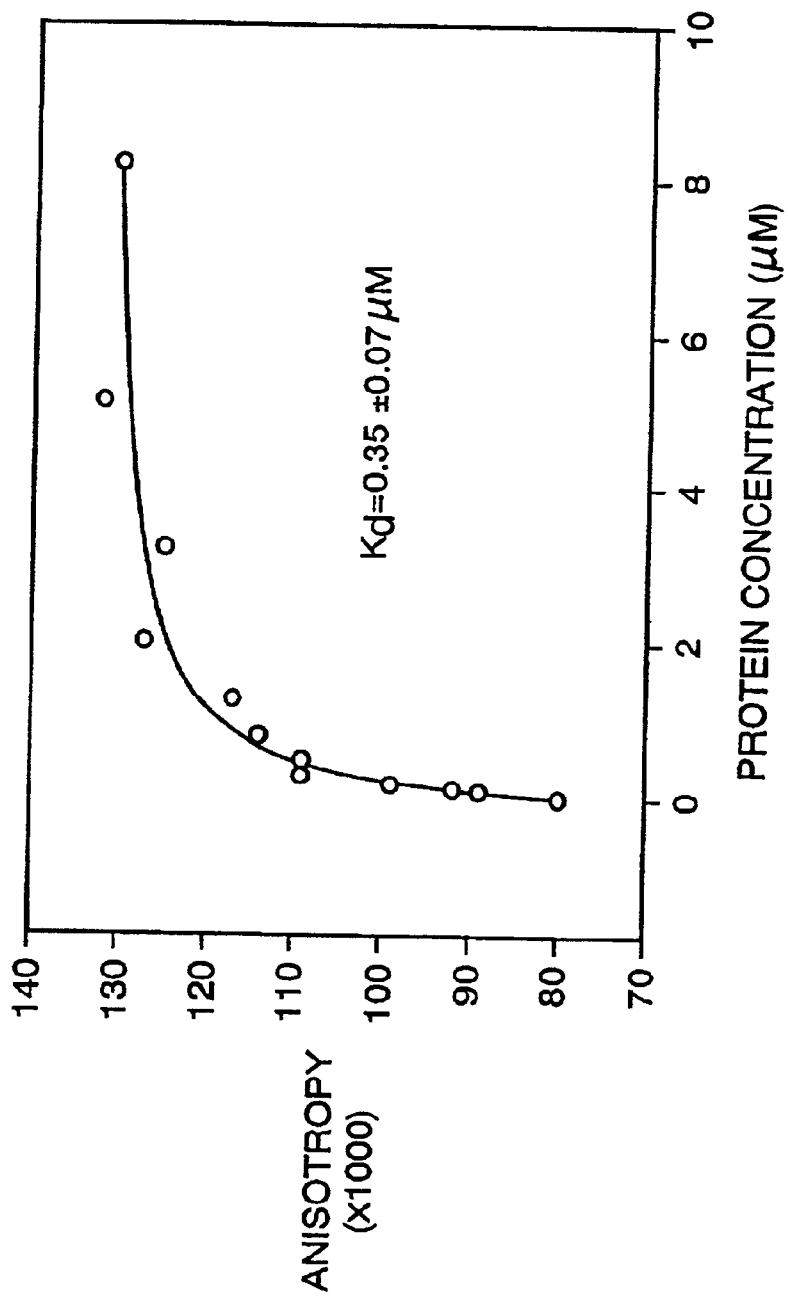
FIG. 3 illustrates the determination of the dissociation constant for synthetic fibrin-binding peptide DX-304 by fluorescence anisotropy.

The fluorescein-labeled peptides (DX-303 and DX-304) were used to determine the equilibrium dissociation constants ($K_D$) for the peptides to DD(E) using fluorescence polarization. FIGS. 2 and 3 show the anisotropy plots for determining dissociation constants for DD(E) binding for DX-303 and DX-304, respectively. DX-303 has a $K_D$ of 500 nM and DX-304 has a $K_D$ of 400 nM. These peptides thus exhibited dissociation constants lower than any previously isolated fibrin binding peptide (cf. DX-101, SEQ ID NO: 14, supra). $K_D$ is related to $k_{off}$ as $K_D = k_{off}/k_{on}$. Because $k_{on}$ can vary between peptides, a lower $K_D$ correlates with (but is not necessarily proportional to) a lower $k_{off}$.

EXAMPLE 5

Testing Imaging Agents Prepared From Isolated Fibrin Binders

To test the ability of the newly discovered peptides as imaging agents, the DX-303 and DX-304 synthetic peptides were labeled with hydrazinonicotinic acid (HYNIC, see Schwartz, et al., *Bioconj. Chem.*, 2, 333 (1991)) to produce DX-328 (SEQ ID NO: 16) and DX-329 (SEQ ID NO: 19). HYNIC is a strong chelator of $^{99m}$Tc. Because HYNIC only occupies one of the coordination sites on Tc, it requires an additional coligand to occupy the other sites. The advantages of HYNIC over other chelators are that the radiolabeled complex is more stable than that for other chelators, and the biodistribution and blood clearance time of the imaging agent can be modified by changing the coligand.

Preliminary imaging experiments were performed with $^{99m}$Tc-labeled DX-328 using tricine as a coligand. A human fibrin gel was formed around a small wire placed in the femoral artery of a rabbit. The radiolabeled imaging agent was injected into the ear vein of the rabbit, and images were taken using a gamma camera.

Figure 4:
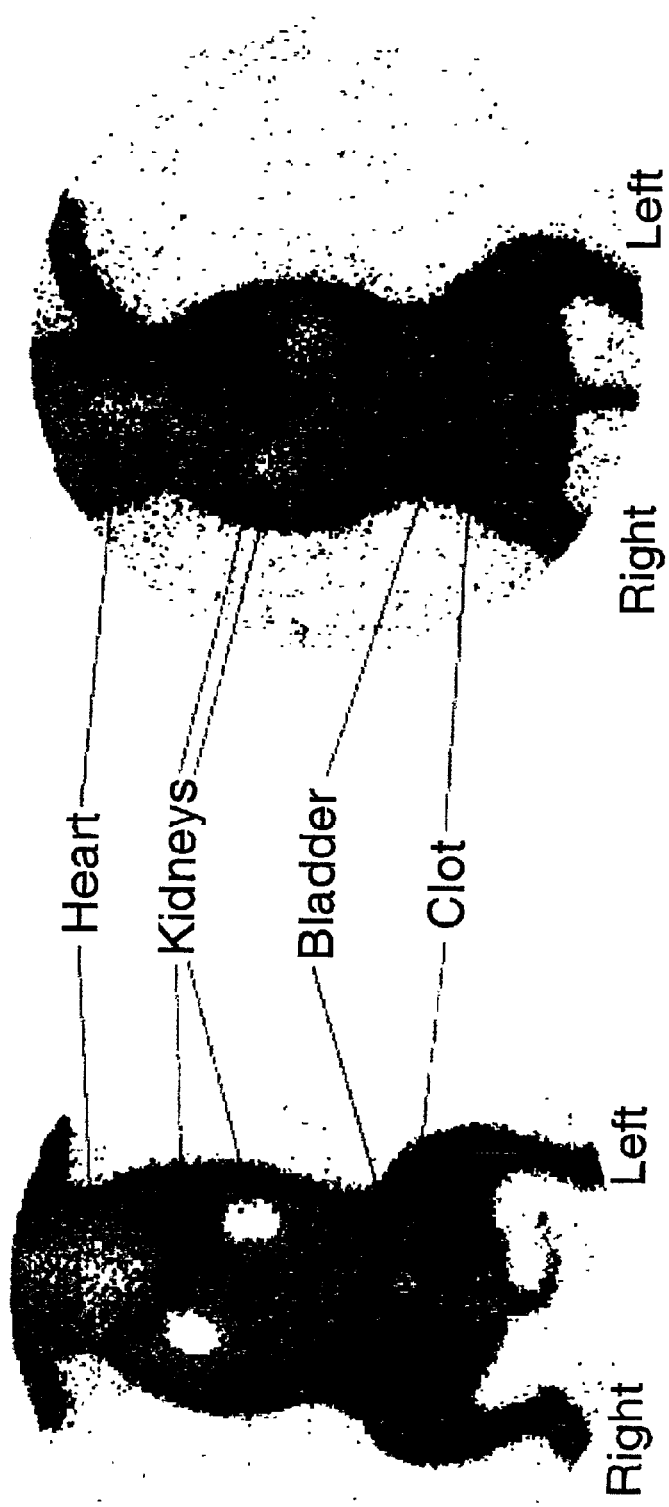
FIG. 4 is a side-by-side comparison of x-ray images of rabbits with artificial fibrin clots visualized using an imaging agent prepared from a radiolabeled peptide according to the invention (DX-328) or commercial x-ray imaging agent (Acutect).

FIG. 4 shows x-ray images of the test rabbit administered DX-328 and another test rabbit administered the commercial imaging agent ACUTECT (Diatide).

Referring to FIG. 4, in the rabbit administered DX-328, the clot in the left thigh (which appears on the right side of the rabbit in this ventral image) can clearly be seen in comparison to the clot-free right thigh. Because the DX-328 that is unbound to the clot is renally excreted from the body, the kidneys and bladder have a high level of activity, as expected. The intensity of radioactivity in the pulmonary region is due to circulating imaging agent that has not yet cleared. By increasing the time between injection and imaging, the background in the pulmonary region and elsewhere should be reduced as the unbound imaging agent clears through the kidneys. Alternatively, the same effect could be achieved by decreasing the clearance time of the imaging agent. This could be accomplished by using EDDA as a coligand instead of tricine.

As a positive control, clot images were obtained in a separate rabbit using ACUTECT. Acutect binds activated platelets, rather than fibrin. Accordingly, a fresh human blood clot was used in place of a fibrin gel for the Acutect imaging experiment. While the Acutect image at 90 minutes post-injection is able to differentiate between the clotted left thigh vs. the clot-free right thigh, the difference is less clear than in the DX-328 image.

EXAMPLE 6

Generation and Screening of a Secondary Library

A secondary library was made using a fibrin binding peptide isolated from the TN-9/IV library as a template. The method of peptide optimization by soft randomization as described in Fairbrother et al., *Biochemistry*, 37:17754–17764 (1998) was used to prepare a library based on the synthetic peptide having the amino acid sequence WQPCPWESWTFCWDP (SEQ. ID. NO: 5). During synthesis of the template DNA used to make the library, at each residue position of the template, a specific nucleotide within a particular codon was substituted. The particular codon was thus allowed to evolve by adding fixed amounts of the other three nucleotides that do not code for the parent codon. The sub-library was produced by maintaining the parent nucleotide within each codon at 70% frequency whereas the other nucleotides were substituted at 10% frequency. Keeping the parent nucleotides in the majority enabled the overall consensus sequence to be maintained. However, upon inspection of the individual isolates, multiple mutations were possible, which allowed selection of peptides with improved binding ability compared to the parent sequence.

Before selecting for phage that bind specifically to fibrin, the secondary library of a total of 2×10$^{11}$ pfu of phage was depleted of phage having an affinity for streptavidin by introducing streptavidin-coated beads. The depleted phage library was mixed with a fibrin target, i.e., human DD(E) biotinylated and immobilized on streptavidin beads, prepared as in Examples 2. After a 2-hour incubation and continuous mixing of the target to allow binding of phage to DD(E), the beads were washed multiple times with wash buffer (TBS, 2 mM Cacl2, 0.05% TWEEN 20) to remove unbound phage.

Collection of bound phage was performed in three steps each using 50 μM of a synthesized peptide corresponding to the template that was used to make the secondary library (i.e., DX-287 (SEQ ID NO: 15)). The first step was kinetic elution for 1 hour at room temperature; the eluted phage were recovered and used to infect cells for amplification. The second step was kinetic elution performed by incubating and mixing the bound phage with fresh peptide at 4° C. overnight; the eluted phage were recovered and used to infect cells for amplification. In the third step, collection the remaining phage (still immobilized on the DD(E) beads) was accomplished by contacting the phage-containing beads with the host cells directly for infection.

Three rounds of selection were performed. Phage plaques from the second and third rounds were picked and analyzed by ELISA and sequencing methods as in Example 3 to detect specific binders of DD(E) to identify a second generation of high affinity fibrin binding peptides. The sequences of fibrin binding peptides isolated from the secondary library are shown in Table 3 below.

The DD(E) positive isolates were assayed for competition against 50 μM and 5 μM free DX-287 peptide. Peptides that showed minimal competition with the parent peptide were deemed higher affinity binders.

TABLE 3

Fibrin binding peptides from a secondary library

| sequence | (template) | SEQ ID NO: |
|---|---|---|
| frequency | WQPCPWESWTFCWDP | 5 |
| 20 | PRPCYGESGIFCWKV | 27 |
| 7 | PRPCTGEPGPICGPR | 28 |

TABLE 3-continued

Fibrin binding peptides from a secondary library

| sequence | (template) | SEQ ID NO: |
|---|---|---|
| 3 | WQACQLGYRTYCWDG | 29 |
| 2 | WKFCDGEPWLFCWDG | 30 |
| 1 | WNGCGWGSWKFCGEG | 31 |
| 1 | WLNCGWGSGKLCLGV | 32 |
| 1 | CYFCPGEPWTFCCDD | 33 |
| 1 | WHFCPGEPWTFCWAG | 34 |
| 1 | WQTCPGYLRSLCWDG | 35 |
| 1 | WYFCPGEPWSFCPDG | 36 |
| 1 | PRPCRGESWPYCWGG | 37 |
| 1 | WQACPGYKRQFCWDR | 38 |
| 1 | PRPCGQESRTFCLEG | 39 |
| 1 | PRPCFQKGGTLCWPG | 40 |

Although a number of embodiments and features have been described above, it will be understood by those skilled in the art that modifications and variations of the described embodiments and features may be made without departing from the teachings of the disclosure or the scope of the invention as defined by the appended claims.

The publications cited herein are incorporated by reference.

What is claimed is:

1. An isolated polypeptide having the ability to bind to fibrin, the polypeptide comprising the amino acid sequence: Cys-$X_2$-$X_3$-$X_4$-$X_5$-$X_6$-$X_7$-$X_8$-Cys (SEQ ID NO: 2), wherein $X_2$ is Pro, Arg, Asn, Asp, Gln, Gly, Phe, Ser, Thr, or Tyr; $X_3$ is Ala, Asn, Asp, Gln, Glu, Gly, Ile, Leu, Met, Phe, Pro, Ser, Thr, Trp, Tyr, or Val; $X_4$ is Glu, Gly, Lys, Ser, or Tyr; $X_5$ is Pro, Asp, Glu, Asn, Gln, Gly, Leu, Lys, Ser, Thr, or Tyr; $X_6$ is Arg, Gly, or Trp; $X_7$ is Leu, Ile, Lys, Met, Asn, Gln, Pro, Ser, Thr, or Val; and $X_8$ is Ile, Leu, Phe, Trp, or Tyr.

2. The polypeptide according to claim 1, comprising the amino acid sequence: Cys-$X_2$-$X_3$-$X_4$-$X_5$-Trp-$X_7$-$X_8$-Cys (SEQ ID NO: 42), wherein $X_2$ is Pro, Asn, Gln, Ser, or Thr; $X_3$ is Ala, Asn, Asp, Gln, Glu, Gly, Ile, Leu, Met, Phe, Pro, Ser, Thr, Trp, Tyr, or Val; $X_4$ is Glu or Ser; $X_5$ is Pro, Asp, Glu, Asn, Gln, Ser, Thr, or Tyr; $X_7$ is Leu, Ile, Met, Asn, Gln, Ser, Thr, or Val; and $X_8$ is Phe, Trp, or Tyr.

3. The polypeptide according to claim 1, wherein $X_2$ is Pro; $X_3$ is Asp, Glu, Gly, Met, or Trp; $X_4$ is Glu; $X_5$ is Asn, Asp, Glu, Pro, or Ser; $X_6$ is Trp; $X_7$ is Leu or Thr; $X_8$ is Phe.

4. The polypeptide according to claim 1, wherein the polypeptide comprises an amino acid sequence selected from the group consisting of:

Cys-Ser-Asp-Glu-Asn-Trp-Leu-Trp-Cys (SEQ ID NO:21);

Cys-Pro-Met-Ser-Glu-Trp-Leu-Tyr-Cys (SEQ ID NO: 22);

Cys-Pro-Trp-Glu-Ser-Trp-Thr-Phe-Cys (SEQ ID NO: 23);

Cys-Gln-Glu-Glu-Pro-Trp-Leu-Phe-Cys (SEQ ID NO: 24);

Cys-Pro-Gly-Glu-Asp-Trp-Leu-Phe-Cys (SEQ ID NO: 25);

Cys-Tyr-Gly-Glu-Ser-Gly-Ile-Phe-Cys (SEQ ID NO:43);

Cys-Thr-Gly-Glu-Pro-Gly-Pro-Ile-Cys (SEQ ID NO:44);

Cys-Gln-Leu-Gly-Tyr-Arg-Thr-Tyr-Cys (SEQ ID NO:45);

Cys-Asp-Gly-Glu-Pro-Trp-Leu-Phe-Cys (SEQ ID NO:46);

Cys-Gly-Trp-Gly-Ser-Trp-Lys-Phe-Cys (SEQ ID NO:47);

Cys-Gly-Trp-Gly-Ser-Gly-Lys-Leu-Cys (SEQ ID NO:48);

Cys-Pro-Gly-Glu-Pro-Trp-Thr-Phe-Cys (SEQ ID NO:49);

Cys-Pro-Gly-Glu-Pro-Trp-Thr-Phe-Cys (SEQ ID NO:50);

Cys-Pro-Gly-Tyr-Leu-Arg-Ser-Leu-Cys (SEQ ID NO: 51);

Cys-Pro-Gly-Glu-Pro-Trp-Ser-Phe-Cys (SEQ ID NO:52);

Cys-Arg-Gly-Glu-Ser-Trp-Pro-Tyr-Cys (SEQ ID NO:53);

Cys-Pro-Gly-Tyr-Lys-Arg-Gln-Phe-Cys (SEQ ID NO:54);

Cys-Gly-Gln-Glu-Ser-Arg-Thr-Phe-Cys (SEQ ID NO:55); and

Cys-Phe-Gln-Lys-Gly-Gly-Thr-Leu-Cys (SEQ ID NO:56).

5. An isolated polypeptide having the ability to bind to fibrin, the polypeptide comprising the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$ (SEQ ID NO:1), wherein $X_1$ is Cys, Pro, or Trp; $X_2$ is Ala, Arg, Asn, Asp, Gln, Glu, Gly, His, Ile, Leu, Lys, Met, Phe, Pro, Ser, Thr, Trp, Tyr or Val, or if $X_4$ and $X_{12}$ are not Cys, then $X_2$ may be Cys; $X_3$ is Ala, Asn, Gln, Gly, Ile, Leu, Met, Phe, Pro, or Thr; $X_4$ is Cys or another amino acid capable of forming a covalent cross-link to $X_{12}$; $X_5$ is Pro, Arg, Asn, Asp, Gln, Gly, Phe, Ser, Thr or Tyr; $X_6$ is Ala, Asn, Asp, Gln, Glu, Gly, Ile, Leu, Met, Phe, Pro, Ser, Thr, Thr, Tyr, or Val; $X_7$ is Glu, Gly, Lys, Ser, or Tyr; $X_8$ is Pro, Asp, Glu, Asn, Gln, Glu, Gly, Leu, Lys, Ser, Thr, or Tyr; $X_9$ is Arg, Gly, or Trp; $X_{10}$ is Leu, Ile, Lys, Met, Asn, Gln, Pro, Ser, Thr, or Val; $X_{11}$ is Ile, Leu, Phe, Trp, or Tyr; $X_{12}$ is Cys or another amino acid capable of forming a covalent cross-link to $X_4$; $X_{13}$ is Cys, Gly, Leu, Phe, Pro, Trp, or Tyr; $X_{14}$ is Pro, Ala, Gly, Asn, Gln, Lys, Ser, Thr, Tyr, Asp, Glu, or His; and $X_{15}$ is Ala, Arg, Asp, Ile, Leu, Met, Phe, Pro, Trp, Val, Asn, Gln, Gly, Ser, Thr, Tyr, or His.

6. The polypeptide according to claim 5, comprising the amino acid sequence: Trp-$X_2$-$X_3$-$X_4$-$X_5$-$X_6$-$X_7$-$X_8$-Trp-$X_{10}$-$X_{11}$-$X_{12}$-$X_{13}$-$X_{14}$-$X_{15}$ ((SEQ ID NO:41), wherein $X_2$ is Ala, Arg, Asn, Asp, Gln, Glu, Gly, His, Ile, Leu, Lys, Met, Phe, Pro, Ser, Thr, Thr, Tyr or Val, or if $X_4$ and $X_{12}$ are not Cys, then $X_2$ may be Cys; $X_3$ is Ala, Asn, Gln, Gly, Ile, Leu, Met, Phe, or Pro; $X_4$ is Cys or another amino acid capable of forming a covalent cross-link to $X_{12}$; $X_5$ is Pro, Asn, Gln, Ser, or Thr; $X_6$ is Ala, Asn, Asp, Gln, Glu, Gly, Ile, Leu, Met, Phe, Pro, Ser, Thr, Trp, Tyr, or Val; $X_7$ is Glu or Ser; $X_8$ is Pro, Asp, Glu, Asn, Gln, Ser, Thr, or Tyr; $X_{10}$ is Leu, Ile, Met, Asn, Gln, Ser, Thr, or Val; $X_{11}$ is Phe, Trp, or Tyr; $X_{12}$ is Cys or another amino acid capable of forming a covalent cross-link to $X_4$; $X_{13}$ is Phe, Trp, or Tyr; $X_{14}$ is Pro, Ala, Gly, Asn, Gln, Ser, Thr, Tyr, Asp, Glu, or His; and $X_{15}$ is Ala, Ile, Leu, Met, Phe, Pro, Trp, Val, Asn, Gln, Gly, Ser, Thr, Tyr, or His.

7. The polypeptide according to claim 6, wherein $X_2$ is Ala, Gln, Glu, Lys, or Met; $X_3$ is Ala, Leu, Met, or Pro; $X_4$ is Cys; $X_5$ is Pro; $X_6$ is Asp, Glu, Gly, Met, or Trp; $X_7$ is Glu; $X_8$ is Asn, Asp, Glu, Pro, or Ser; $X_{10}$ is Leu or Thr; $X_{11}$ is Phe; $X_{12}$ is Cys; $X_{13}$ is Trp; $X_{14}$ is Asp, Gly, His, Phe, or Ser; and $X_{15}$ is Ala, Gly, His, Pro, or Ser.

8. The polypeptide according to claim 7, wherein the amino acid residue $X_{10}$ is Leu.

9. The polypeptide according to claim 5, wherein the polypeptide comprises an amino acid sequence selected from the group consisting of:

Trp-Glu-Leu-Cys-Ser-Asp-Glu-Asn-Trp-Leu-Trp-Cys-Trp-Pro-His (SEQ ID NO: 3);

Trp-Met-Met-Cys-Pro-Met-Ser-Glu-Trp-Leu-Tyr-Cys-Trp-Ser-Ala (SEQ ID NO: 4);

Trp-Gln-Pro-Cys-Pro-Trp-Glu-Ser-Trp-Thr-Phe-Cys-Trp-Asp-Pro (SEQ ID NO: 5);

Trp-Ala-Pro-Cys-Gln-Glu-Glu-Pro-Trp-Leu-Phe-Cys-Phe-His-Gly (SEQ ID NO: 6);

Trp-Lys-Ala-Cys-Pro-Gly-Glu-Asp-Trp-Leu-Phe-Cys-Trp-Gly-Ser (SEQ ID NO: 7);

Pro-Arg-Pro-Cys-Tyr-Gly-Glu-Ser-Gly-Ile-Phe-Cys-Trp-Lys-Val (SEQ ID NO:27);

Pro-Arg-Pro-Cys-Thr-Gly-Glu-Pro-Gly-Pro-Ile-Cys-Gly-Pro-Arg (SEQ ID NO:28);

Trp-Gln-Ala-Cys-Gln-Leu-Gly-Tyr-Arg-Thr-Tyr-Cys-Trp-Asp-Gly (SEQ ID NO:29);

Trp-Lys-Phe-Cys-Asp-Gly-Glu-Pro-Trp-Leu-Phe-Cys-Trp-Asp-Gly (SEQ ID NO:30);

Trp-Asn-Gly-Cys-Gly-Trp-Gly-Ser-Trp-Lys-Phe-Cys-Gly-Glu-Gly (SEQ ID NO:31);

Trp-Leu-Asn-Cys-Gly-Trp-Gly-Ser-Gly-Lys-Leu-Cys-Leu-Gly-Val (SEQ ID NO:32);

Cys-Tyr-Phe-Cys-Pro-Gly-Glu-Pro-Trp-Thr-Phe-Cys-Cys-Asp-Asp (SEQ ID NO:33);

Trp-His-Phe-Cys-Pro-Gly-Glu-Pro-Trp-Thr-Phe-Cys-Trp-Ala-Gly (SEQ ID NO:34);

Trp-Gln-Thr-Cys-Pro-Gly-Tyr-Leu-Arg-Ser-Leu-Cys-Trp-Asp-Gly (SEQ ID NO:35);

Trp-Tyr-Phe-Cys-Pro-Gly-Glu-Pro-Trp-Ser-Phe-Cys-Pro-Asp-Gly (SEQ ID NO:36);

Pro-Arg-Pro-Cys-Arg-Gly-Glu-Ser-Trp-Pro-Tyr-Cys-Trp-Gly-Gly (SEQ ID NO:37);

Trp-Gln-Ala-Cys-Pro-Gly-Tyr-Lys-Arg-Gln-Phe-Cys-Trp-Asp-Arg (SEQ ID NO:38);

Pro-Arg-Pro-Cys-Gly-Gln-Glu-Ser-Arg-Thr-Phe-Cys-Leu-Glu-Gly (SEQ ID NO:39); and

Pro-Arg-Pro-Cys-Phe-Gln-Lys-Gly-Gly-Thr-Leu-Cys-Trp-Pro-Gly (SEQ ID NO:40).

10. A method of detecting fibrin in a mammalian subject comprising the steps of: (a) detectably labeling a polypeptide according to any one of claims 1–4 or 5–9; (b) administering to said subject the labeled polypeptide and, thereafter, (c) detecting the labeled polypeptide in the subject.

11. The method according to claim 10, wherein said label is fluorescent, echogenic, radioactive, or paramagnetic.

12. The method according to claim 10, wherein said label is $^{111}$In or $^{99m}$Tc.

13. The method of according to claim 10, wherein said detecting step is indicative of deep-vein thrombosis, pulmonary embolism, cardiogenic thrombosis, atherosclerosis, or stroke.

14. A method of treating a disease involving thrombus formation, comprising the step: administering to a mammalian subject in need of treatment for such a disease a composition comprising a polypeptide according to any one of claims 1–4 or 5–9 conjugated with a pharmaceutical effective for treating said disease involving thrombus formation.

15. The method according to claim 14, wherein said disease is deep-vein thrombosis, pulmonary embolism, cardiogenic thrombosis, atherosclerosis, myocardial infarct, reperfusion ischemia, or stroke.

16. The method according to claim 14, wherein said pharmaceutical is a thrombolytic agent selected from tPA, streptokinase, and urokinase.

17. A recombinant host cell or bacteriophage expression on its surface an exogenous fibrin binding polypeptide according to any one of claims 1–4 or 5–9.

18. A magnetic resonance imaging contrast agent comprising at least one paramagnetic metal atom linked to at least one polypeptide according to any one of claims 1–4 or 5–9.

19. The magnetic resonance imaging contrast agent according to claim 18, wherein said magnetic resonance imaging contrast agent further comprises at least one chelator selected from the group consisting of diethylenetriaminepentaacetic acid, 1,4,7,10-tetraazacyclotetradecane-1,4,7,10-tetraacetic acid, ethylenediaminetetraacetic acid, 1,4,8,11-tetraazacyclotetradecane-1,4,8,11-tetraacetic acid, ethylenebis-(2-hydroxyphenylglycine), bis-2 (hydroxybenzyl)-ethylene-diaminediacetic acid, 1,4,7-triazacyclononane N,N',N"-triacetic acid, 1,4,7,10-tetraazacyclotetradecane-1,4,7,10-tetra(methyl tetraacetic acid), 1,4,8,11-tetraazacyclotetradecane-1,4,8,11-(methyl tetraacetic acid), 1,3-propylenediaminetetraaceticacid, triethylenetetraaminehexaacetic acid, 1,5,10-N,N',N"-tris(2,3-dihydroxybenzoyl)-tricatecholate, and 1,3,5-N,N',N"-tris(2,3-dihydroxybenzoyl) aminomethylbenzene.

20. The magnetic resonance imaging contrast agent according to claim 19, wherein said chelator comprises diethylenetriamine or tetraazacyclododecane or a carboxymethyl-substituted derivative thereof.

21. The magnetic resonance imaging contrast agent according to claim 19, wherein said paramagnetic metal atom is selected from the group consisting of: $Mn^{2+}$, $Cu^{2+}$, $Fe^{2+}$, $Co^{2+}$, $Ni^{2+}$, $Gd^{3+}$, $Eu^{3+}$, $Dy^{3+}$, $Pr^{3+}$, $Cr^{3+}$, $Co^{3+}$, $Fe^{3+}$, $Ti^{3+}$, $Tb^{3+}$, $Nd^{3+}$, $Sm^{3+}$, $Ho^{3+}$, $Er^{3+}$, $Pa^{4+}$, and $Eu^{2+}$.

22. The magnetic resonance imaging contrast agent according to claim 21, wherein said paramagnetic metal atom is $Gd^{3+}$.

23. A method for identifying fibrin binding compounds comprising the steps of utilizing a fibrin binding polypeptide according to any one of claims 1–4 or 5–9 to form a complex with a fibrin target, contacting said complex with one or more potential fibrin binding compounds, and determining whether said one or more potential fibrin binding compounds competes with said fibrin binding polypeptide to form a complex with said fibrin target.

24. A method for identifying fibrin binding compounds comprising the steps of contacting a solution containing a potential fibrin binding compound with fibrin target to form a complex between said compound and the fibrin target, contacting said complex with a fibrin binding polypeptide according to any one of claims 1–4 or 5–9, and determining whether said fibrin binding polypeptide competes with said potential fibrin binding compound to form a complex with said fibrin target.

25. A diagnostic imaging agent comprising a polypeptide according to any one of claims 1–4 or 5–9 linked to a detectable label.

26. The imaging agent according to claim 25, wherein said polypeptide is radiolabeled.

27. The imaging agent according to claim 25, wherein said polypeptide is labeled with $^{99m}$Tc.

28. The imaging agent according to claim 25, wherein said polypeptide is fluoresceinated.

29. The imaging agent according to claim 25, wherein said polypeptide is linked to an echogenic label suitable for ultrasound imaging.

30. A method of medical imaging comprising the steps of administering to a mammalian subject a pharmaceutical preparation of a contrast agent comprising at least one polypeptide according to any one of claims 1–4 or 5–9 and imaging said contrast agent by a step selected from the group consisting of magnetic resonance imaging, ultrasound imaging, optical imaging, sonoluminescence imaging, photoacoustic imaging, and nuclear imaging.

31. The method of medical imaging according to claim 30, wherein said administering step is selected from among the group consisting of: inhaling, transdermal absorbing, intramuscular injecting, subcutaneous injecting, intravenous injecting, and intra-arterial injecting.

32. The method of medical imaging according to claim 30, wherein said pharmaceutical preparation is packaged in a container selected from among the group consisting of: kit, syringe, vial, bottle, flexible container, packet, or inhaler.

33. A method of purifying fibrin or fibrin-like polypeptide from a solution containing it comprising contacting the solution with at least one polypeptide according to any one of claims 1–4 or 5–9, and then separating said polypeptide from said solution.

34. The polypeptide according to claim 3, wherein the polypeptide comprises the sequence Cys-Pro-Trp-Glu-Ser-Trp-Thr-Phe-Cys (SEQ ID NO: 23).

35. The polypeptide according to claim 3, wherein the polypeptide comprises the sequence Trp-Gln-Pro-Cys-Pro-Trp-Glu-Ser-Trp-Thr-Phe-Cys-Trp-Asp-Pro (SEQ ID NO: 5).

36. The polypeptide according to claim 3, wherein $X_2$ is Pro.

37. The polypeptide according to claim 3, wherein $X_3$ is Asp, Glu, Gly, Met, or Trp.

38. The polypeptide according to claim 3, wherein $X_4$ is Glu.

39. The polypeptide according to claim 3, wherein $X_5$ is Asn, Asp, Glu, Pro, or Ser.

40. The polypeptide according to claim 3, wherein $X_6$ is Trp.

41. The polypeptide according to claim 3, wherein $X_7$ is Leu or Thr.

42. The polypeptide according to claim 3, wherein $X_8$ is Phe.

43. The polypeptide according to claim 6, wherein $X_2$ is Ala, Gln, Glu, Lys, or Met.

44. The polypeptide according to claim 6, wherein $X_3$ is Ala, Leu, Met, or Pro.

45. The polypeptide according to claim 6, wherein $X_4$ is Cys.

46. The polypeptide according to claim 6, wherein $X_5$ is Pro.

47. The polypeptide according to claim 6, wherein $X_6$ is Asp, Glu, Gly, Met, or Trp.

48. The polypeptide according to claim 6, wherein $X_7$ is Glu.

49. The polypeptide according to claim 6, wherein $X_8$ is Asn, Asp, Glu, Pro, or Ser.

50. The polypeptide according to claim 6, wherein $X_{10}$ is Leu or Thr.

51. The polypeptide according to claim 6, wherein $X_{11}$ is Phe.

52. The polypeptide according to claim 6, wherein $X_{12}$ is Cys.

53. The polypeptide according to claim 6, wherein $X_{13}$ is Trp.

54. The polypeptide according to claim 6, wherein $X_{14}$ is Asp, Gly, His, Phe, or Ser.

55. The polypeptide according to claim 6, wherein $X_{15}$ is Ala, Gly, His, Pro, or Ser.

56. The polypeptide according to claim 6, wherein $X_{10}$ is Leu.

57. The polypeptide according to claim 6, wherein $X_3$ is Pro.

58. The polypeptide according to claim 6, wherein $X_{11}$ is Phe.

59. The polypeptide according to claim 6, wherein $X_{13}$ is Trp or Phe.

* * * * *

SEQUENCE LISTING

```
<160> NUMBER OF SEQ ID NOS: 56

<210> SEQ ID NO 1
<211> LENGTH: 15
<212> TYPE: PRT
<213> ORGANISM: Artificial Sequence
<220> FEATURE:
<223> OTHER INFORMATION: fibrin binding polypeptides
<221> NAME/KEY: MISC_FEATURE
<222> LOCATION: (1)..(1)
<223> OTHER INFORMATION: X1 is Cys, Pro, or Trp
<221> NAME/KEY: MISC_FEATURE
<222> LOCATION: (2)..(2)
<223> OTHER INFORMATION: X2 is Ala, Arg, Asn, Asp, Gln, Glu, Gly, His,
      Ile, Leu, Lys, Met,Phe, Pro, Ser, Thr, Trp, Tyr or Val, or if X4
      and X12 are not Cys, then X2 may be Cys
<221> NAME/KEY: MISC_FEATURE
<222> LOCATION: (3)..(3)
<223> OTHER INFORMATION: X3 is Ala, Asn, Gln, Gly, Ile, Leu, Met, Phe,
      Pro, or Thr
<221> NAME/KEY: MISC_FEATURE
<222> LOCATION: (4)..(4)
<223> OTHER INFORMATION: X4 is Cys or another amino acid capable of
      forming a covalent cross-link to X12
<221> NAME/KEY: MISC_FEATURE
<222> LOCATION: (5)..(5)
<223> OTHER INFORMATION: X5 is Pro, Arg, Asn, Asp, Gln, Gly, Phe, Ser,
      Thr or Tyr
<221> NAME/KEY: MISC_FEATURE
<222> LOCATION: (6)..(6)
<223> OTHER INFORMATION: X6 is Ala, Asn, Asp, Gln, Glu, Gly, Ile, Leu,
```

```
        Met, Phe, Pro, Ser,Thr, Trp, Tyr, or Val
<221> NAME/KEY: MISC_FEATURE
<222> LOCATION: (7)..(7)
<223> OTHER INFORMATION: X7 is Glu, Gly, Lys, Ser, or Tyr
<221> NAME/KEY: MISC_FEATURE
<222> LOCATION: (8)..(8)
<223> OTHER INFORMATION: X8 is Pro, Asp, Glu, Asn, Gln, Glu, Gly, Leu,
        Lys, Ser, Thr, or Tyr
<221> NAME/KEY: MISC_FEATURE
<222> LOCATION: (9)..(9)
<223> OTHER INFORMATION: X9 is Arg, Gly, or Trp
<221> NAME/KEY: MISC_FEATURE
<222> LOCATION: (10)..(10)
<223> OTHER INFORMATION: X10 is Leu, Ile, Lys, Met, Asn, Gln, Pro, Ser,
        Thr, or Val
<221> NAME/KEY: MISC_FEATURE
<222> LOCATION: (11)..(11)
<223> OTHER INFORMATION: X11 is Ile, Leu, Phe, Trp, or Tyr
<221> NAME/KEY: MISC_FEATURE
<222> LOCATION: (12)..(12)
<223> OTHER INFORMATION: X12 is Cys or another amino acid capable of
        forming a covalent cross-link to X4
<221> NAME/KEY: MISC_FEATURE
<222> LOCATION: (13)..(13)
<223> OTHER INFORMATION: X13 is Cys, Gly, Leu, Phe, Pro, Trp, or Tyr
<221> NAME/KEY: MISC_FEATURE
<222> LOCATION: (14)..(14)
<223> OTHER INFORMATION: X14 is Pro, Ala, Gly, Asn, Gln, Lys, Ser, Thr,
        Tyr, Asp, Glu, or His
<221> NAME/KEY: MISC_FEATURE
<222> LOCATION: (15)..(15)
<223> OTHER INFORMATION: X15 is Ala, Arg, Asp, Ile, Leu, Met, Phe, Pro,
        Trp, Val, Asn, Gln, Gly, Ser, Thr, Tyr, or His

<400> SEQUENCE: 1

Xaa Xaa Xaa Xaa Xaa Xaa Xaa Xaa Xaa Xaa Xaa Xaa Xaa Xaa Xaa
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: fibrin binding polypeptides
<221> NAME/KEY: MISC_FEATURE
<222> LOCATION: (2)..(2)
<223> OTHER INFORMATION: X2 is Pro, Arg, Asn, Asp, Gln, Gly, Phe, Ser,
        Thr or Tyr
<221> NAME/KEY: MISC_FEATURE
<222> LOCATION: (3)..(3)
<223> OTHER INFORMATION: X3 is Ala, Asn, Asp, Gln, Glu, Gly, Ile, Leu,
        Met, Phe, Pro, Ser,Thr, Trp, Tyr, or Val
<221> NAME/KEY: MISC_FEATURE
<222> LOCATION: (4)..(4)
<223> OTHER INFORMATION: X4 is Glu, Gly, Lys, Ser, or Tyr
<221> NAME/KEY: MISC_FEATURE
<222> LOCATION: (5)..(5)
<223> OTHER INFORMATION: X5 is Pro, Asp, Glu, Asn, Gln, Glu, Gly, Leu,
        Lys, Ser, Thr, or Tyr
<221> NAME/KEY: MISC_FEATURE
<222> LOCATION: (6)..(6)
<223> OTHER INFORMATION: X6 is Arg, Gly, or Trp
<221> NAME/KEY: MISC_FEATURE
<222> LOCATION: (7)..(7)
<223> OTHER INFORMATION: X7 is Leu, Ile, Lys, Met, Asn, Gln, Pro, Ser,
        Thr, or Val
<221> NAME/KEY: MISC_FEATURE
<222> LOCATION: (8)..(8)
<223> OTHER INFORMATION: X8 is Ile, Leu, Phe, Trp, or Tyr

<400> SEQUENCE: 2

Cys Xaa Xaa Xaa Xaa Xaa Xaa Xaa Cys
1               5

<210> SEQ ID NO 3
```

```
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 3

Trp Glu Leu Cys Ser Asp Glu Asn Trp Leu Trp Cys Trp Pro His
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 4

Trp Met Met Cys Pro Met Ser Glu Trp Leu Tyr Cys Trp Ser Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 5

Trp Gln Pro Cys Pro Trp Glu Ser Trp Thr Phe Cys Trp Asp Pro
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 6

Trp Ala Pro Cys Gln Glu Glu Pro Trp Leu Phe Cys Phe His Gly
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 7

Trp Lys Ala Cys Pro Gly Glu Asp Trp Leu Phe Cys Trp Gly Ser
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: fibrin binding polypeptide

<400> SEQUENCE: 8

Arg Ala Pro Cys Asp Tyr Tyr Gly Thr Cys Val Glu Leu
1               5                   10

<210> SEQ ID NO 9
<211> LENGTH: 13
```

```
<212> TYPE: PRT
<213> ORGANISM: Artificial Sequence
<220> FEATURE:
<223> OTHER INFORMATION: template of display peptide for phage display
      library
<221> NAME/KEY: MISC_FEATURE
<222> LOCATION: (1)..(3)
<223> OTHER INFORMATION: Xaa1, Xaa2, Xaa3 are independently variable and
      may be any amino acid except cysteine
<221> NAME/KEY: MISC_FEATURE
<222> LOCATION: (5)..(9)
<223> OTHER INFORMATION: Xaa5, Xaa6, Xaa7, Xaa8, Xaa9 are independently
      variable and may be any amino acid except cysteine
<221> NAME/KEY: MISC_FEATURE
<222> LOCATION: (11)..(13)
<223> OTHER INFORMATION: Xaa11, Xaa12, Xaa13 are independently variable
      and may be any amino acid except cysteine

<400> SEQUENCE: 9

Xaa Xaa Xaa Cys Xaa Xaa Xaa Xaa Xaa Cys Xaa Xaa Xaa
1               5                   10

<210> SEQ ID NO 10
<211> LENGTH: 14
<212> TYPE: PRT
<213> ORGANISM: Artificial Sequence
<220> FEATURE:
<223> OTHER INFORMATION: template of display peptide for phage display
      library
<221> NAME/KEY: MISC_FEATURE
<222> LOCATION: (1)..(3)
<223> OTHER INFORMATION: Xaa1, Xaa2, Xaa3 are independently variable and
      may be any amino acid except cysteine
<221> NAME/KEY: MISC_FEATURE
<222> LOCATION: (5)..(10)
<223> OTHER INFORMATION: Xaa5, Xaa6, Xaa7, Xaa8, Xaa9, Xaa10 are
      independently variable and may be any amino acid
      except cysteine
<221> NAME/KEY: MISC_FEATURE
<222> LOCATION: (12)..(14)
<223> OTHER INFORMATION: Xaa12, Xaa13, Xaa14 are independently variable
      and may be any amino acid except cysteine

<400> SEQUENCE: 10

Xaa Xaa Xaa Cys Xaa Xaa Xaa Xaa Xaa Xaa Cys Xaa Xaa Xaa
1               5                   10

<210> SEQ ID NO 11
<211> LENGTH: 15
<212> TYPE: PRT
<213> ORGANISM: Artificial Sequence
<220> FEATURE:
<223> OTHER INFORMATION: template for display peptide of a phage display
      library
<221> NAME/KEY: MISC_FEATURE
<222> LOCATION: (1)..(3)
<223> OTHER INFORMATION: Xaa1, Xaa2, Xaa3 are independently variable and
      may be any amino acid except cysteine
<221> NAME/KEY: MISC_FEATURE
<222> LOCATION: (5)..(11)
<223> OTHER INFORMATION: Xaa5, Xaa6, Xaa7, Xaa8, Xaa9, Xaa10, Xaa11 are
      independently variable and may be any amino acid
      except cysteine
<221> NAME/KEY: MISC_FEATURE
<222> LOCATION: (13)..(15)
<223> OTHER INFORMATION: Xaa13, Xaa14, Xaa15 are independently variable
      and may be any amino acid except cysteine

<400> SEQUENCE: 11

Xaa Xaa Xaa Cys Xaa Xaa Xaa Xaa Xaa Xaa Xaa Cys Xaa Xaa Xaa
1               5                   10                  15

<210> SEQ ID NO 12
```

```
<211> LENGTH: 7
<212> TYPE: PRT
<213> ORGANISM: Artificial Sequence
<220> FEATURE:
<223> OTHER INFORMATION: 7-mer fibrin binding loop

<400> SEQUENCE: 12

Cys Asp Tyr Tyr Gly Thr Cys
1               5

<210> SEQ ID NO 13
<211> LENGTH: 12
<212> TYPE: PRT
<213> ORGANISM: Artificial Sequence
<220> FEATURE:
<223> OTHER INFORMATION: template of display peptide for phage display
      library
<221> NAME/KEY: MISC_FEATURE
<222> LOCATION: (1)..(1)
<223> OTHER INFORMATION: Xaa1 is Ala, Asp, Phe, Gly, His, Leu, Asn, Pro,
      Gln, Arg, Ser, Val, Trp or Tyr
<221> NAME/KEY: MISC_FEATURE
<222> LOCATION: (2)..(3)
<223> OTHER INFORMATION: Xaa2, Xaa3 are independently Ala, Asp, Glu, Phe
      ,Gly, His, Lys, Leu, Met, Asn, Pro, Gln, Arg, Ser,
      Thr, Val, Trp or Tyr
<221> NAME/KEY: MISC_FEATURE
<222> LOCATION: (5)..(8)
<223> OTHER INFORMATION: Xaa5, Xaa6, Xaa7, Xaa8 are independently Ala,
      Asp,Glu, Phe, Gly, His, Lys, Leu, Met, Asn, Pro, Gln,
      Arg, Ser, Thr, Val, Trp or Tyr
<221> NAME/KEY: MISC_FEATURE
<222> LOCATION: (10)..(11)
<223> OTHER INFORMATION: Xaa10, Xaa11 are independently Ala, Asp, Glu,
      Phe,Gly, His, Lys, Leu, Met, Asn, Pro, Gln, Arg, Ser,
      Thr, Val, Trp or Tyr
<221> NAME/KEY: MISC_FEATURE
<222> LOCATION: (12)..(12)
<223> OTHER INFORMATION: Xaa12 is Ala, Asp, Phe, Gly, His, Leu, Asn, Pro
      ,Gln, Arg, Ser, Val, Trp or Tyr

<400> SEQUENCE: 13

Xaa Xaa Xaa Cys Xaa Xaa Xaa Xaa Cys Xaa Xaa Xaa
1               5                   10

<210> SEQ ID NO 14
<211> LENGTH: 22
<212> TYPE: PRT
<213> ORGANISM: Artificial Sequence
<220> FEATURE:
<223> OTHER INFORMATION: DX-101 fibrin binding polypeptide

<400> SEQUENCE: 14

Ala Glu Gly Thr Gly Ser Gln Trp Glu Cys Pro Tyr Gly Leu Cys Trp
1               5                   10                  15

Ile Gln Ala Pro Gly Lys
            20

<210> SEQ ID NO 15
<211> LENGTH: 19
<212> TYPE: PRT
<213> ORGANISM: Artificial Sequence
<220> FEATURE:
<223> OTHER INFORMATION: slow dissociating fibrin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (19)..(19)
<223> OTHER INFORMATION: AMIDATION

<400> SEQUENCE: 15
```

-continued

Trp Gln Pro Cys Pro Trp Glu Ser Trp Thr Phe Cys Trp Asp Pro Gly
1               5                   10                  15

Gly Gly Lys

<210> SEQ ID NO 16
<211> LENGTH: 19
<212> TYPE: PRT
<213> ORGANISM: Artificial Sequence
<220> FEATURE:
<223> OTHER INFORMATION: slow dissociating fibrin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (19)..(19)
<223> OTHER INFORMATION: conjugated with HYNIC chelator for Tc
<221> NAME/KEY: MOD_RES
<222> LOCATION: (19)..(19)
<223> OTHER INFORMATION: AMIDATION

<400> SEQUENCE: 16

Trp Gln Pro Cys Pro Trp Glu Ser Trp Thr Phe Cys Trp Asp Pro Gly
1               5                   10                  15

Gly Gly Lys

<210> SEQ ID NO 17
<211> LENGTH: 19
<212> TYPE: PRT
<213> ORGANISM: Artificial Sequence
<220> FEATURE:
<223> OTHER INFORMATION: slow dissociating fibrin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (19)..(19)
<223> OTHER INFORMATION: AMIDATION
<221> NAME/KEY: MOD_RES
<222> LOCATION: (19)..(19)
<223> OTHER INFORMATION: fluoresceinated

<400> SEQUENCE: 17

Trp Gln Pro Cys Pro Trp Glu Ser Trp Thr Phe Cys Trp Asp Pro Gly
1               5                   10                  15

Gly Gly Lys

<210> SEQ ID NO 18
<211> LENGTH: 19
<212> TYPE: PRT
<213> ORGANISM: Artificial Sequence
<220> FEATURE:
<223> OTHER INFORMATION: slow dissociating fibrin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (19)..(19)
<223> OTHER INFORMATION: AMIDATION

<400> SEQUENCE: 18

Trp Ala Pro Cys Gln Glu Glu Pro Trp Leu Phe Cys Phe His Gly Gly
1               5                   10                  15

Gly Gly Lys

<210> SEQ ID NO 19
<211> LENGTH: 19
<212> TYPE: PRT

```
<213> ORGANISM: Artificial Sequence
<220> FEATURE:
<223> OTHER INFORMATION: slow dissociating fibrin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (19)..(19)
<223> OTHER INFORMATION: AMIDATION
<221> NAME/KEY: MOD_RES
<222> LOCATION: (19)..(19)
<223> OTHER INFORMATION: conjugated with HYNIC chelator for Tc

<400> SEQUENCE: 19

Trp Ala Pro Cys Gln Glu Glu Pro Trp Leu Phe Cys Phe His Gly Gly
1               5                   10                  15

Gly Gly Lys

<210> SEQ ID NO 20
<211> LENGTH: 19
<212> TYPE: PRT
<213> ORGANISM: Artificial Sequence
<220> FEATURE:
<223> OTHER INFORMATION: slow dissociating fibrin binding peptide
<221> NAME/KEY: MOD_RES
<222> LOCATION: (1)..(1)
<223> OTHER INFORMATION: ACETYLATION
<221> NAME/KEY: MOD_RES
<222> LOCATION: (19)..(19)
<223> OTHER INFORMATION: AMIDATION
<221> NAME/KEY: MOD_RES
<222> LOCATION: (19)..(19)
<223> OTHER INFORMATION: fluoresceinated

<400> SEQUENCE: 20

Trp Ala Pro Cys Gln Glu Glu Pro Trp Leu Phe Cys Phe His Gly Gly
1               5                   10                  15

Gly Gly Lys

<210> SEQ ID NO 21
<211> LENGTH: 9
<212> TYPE: PRT
<213> ORGANISM: Artificial Sequence
<220> FEATURE:
<223> OTHER INFORMATION: fibrin binding loop

<400> SEQUENCE: 21

Cys Ser Asp Glu Asn Trp Leu Trp Cys
1               5

<210> SEQ ID NO 22
<211> LENGTH: 9
<212> TYPE: PRT
<213> ORGANISM: Artificial Sequence
<220> FEATURE:
<223> OTHER INFORMATION: fibrin binding loop

<400> SEQUENCE: 22

Cys Pro Met Ser Glu Trp Leu Tyr Cys
1               5

<210> SEQ ID NO 23
<211> LENGTH: 9
<212> TYPE: PRT
<213> ORGANISM: Artificial Sequence
<220> FEATURE:
<223> OTHER INFORMATION: fibrin binding loop

<400> SEQUENCE: 23
```

```
Cys Pro Trp Glu Ser Trp Thr Phe Cys
1               5

<210> SEQ ID NO 24
<211> LENGTH: 9
<212> TYPE: PRT
<213> ORGANISM: Artificial Sequence
<220> FEATURE:
<223> OTHER INFORMATION: fibrin binding loop

<400> SEQUENCE: 24

Cys Gln Glu Glu Pro Trp Leu Phe Cys
1               5

<210> SEQ ID NO 25
<211> LENGTH: 9
<212> TYPE: PRT
<213> ORGANISM: Artificial Sequence
<220> FEATURE:
<223> OTHER INFORMATION: fibrin binding loop

<400> SEQUENCE: 25

Cys Pro Gly Glu Asp Trp Leu Phe Cys
1               5

<210> SEQ ID NO 26
<211> LENGTH: 7
<212> TYPE: PRT
<213> ORGANISM: Artificial Sequence
<220> FEATURE:
<223> OTHER INFORMATION: fibrin binding loop

<400> SEQUENCE: 26

Cys Asp Tyr Tyr Gly Thr Cys
1               5

<210> SEQ ID NO 27
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 27

Pro Arg Pro Cys Tyr Gly Glu Ser Gly Ile Phe Cys Trp Lys Val
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 28

Pro Arg Pro Cys Thr Gly Glu Pro Gly Pro Ile Cys Gly Pro Arg
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 29
```

Trp Gln Ala Cys Gln Leu Gly Tyr Arg Thr Tyr Cys Trp Asp Gly
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 30

Trp Lys Phe Cys Asp Gly Glu Pro Trp Leu Phe Cys Trp Asp Gly
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 31

Trp Asn Gly Cys Gly Trp Gly Ser Trp Lys Phe Cys Gly Glu Gly
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 32

Trp Leu Asn Cys Gly Trp Gly Ser Gly Lys Leu Cys Leu Gly Val
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 33

Cys Tyr Phe Cys Pro Gly Glu Pro Trp Thr Phe Cys Cys Asp Asp
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 34

Trp His Phe Cys Pro Gly Glu Pro Trp Thr Phe Cys Trp Ala Gly
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 35

Trp Gln Thr Cys Pro Gly Tyr Leu Arg Ser Leu Cys Trp Asp Gly

<210> SEQ ID NO 36
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 36

```
Trp Tyr Phe Cys Pro Gly Glu Pro Trp Ser Phe Cys Pro Asp Gly
1               5                   10                  15
```

<210> SEQ ID NO 37
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 37

```
Pro Arg Pro Cys Arg Gly Glu Ser Trp Pro Tyr Cys Trp Gly Gly
1               5                   10                  15
```

<210> SEQ ID NO 38
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 38

```
Trp Gln Ala Cys Pro Gly Tyr Lys Arg Gln Phe Cys Trp Asp Arg
1               5                   10                  15
```

<210> SEQ ID NO 39
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 39

```
Pro Arg Pro Cys Gly Gln Glu Ser Arg Thr Phe Cys Leu Glu Gly
1               5                   10                  15
```

<210> SEQ ID NO 40
<211> LENGTH: 15
<212> TYPE: PRT
<213> ORGANISM: Artificial Sequence
<220> FEATURE:
<223> OTHER INFORMATION: fibrin binding polypeptide

<400> SEQUENCE: 40

```
Pro Arg Pro Cys Phe Gln Lys Gly Gly Thr Leu Cys Trp Pro Gly
1               5                   10                  15
```

<210> SEQ ID NO 41
<211> LENGTH: 15
<212> TYPE: PRT
<213> ORGANISM: Artificial Sequence
<220> FEATURE:
<223> OTHER INFORMATION: fibrin binding polypeptides
<221> NAME/KEY: MISC_FEATURE
<222> LOCATION: (2)..(2)
<223> OTHER INFORMATION: X2 is Ala, Arg, Asn, Asp, Gln, Glu, Gly, His, Ile, Leu, Lys, Met,Phe, Pro, Ser, Thr, Trp, Tyr or Val, or if X4 and X12 are not Cys, then X2 may be Cys

```
<221> NAME/KEY: MISC_FEATURE
<222> LOCATION: (3)..(3)
<223> OTHER INFORMATION: X3 is Ala, Asn, Gln, Gly, Ile, Leu, Met, Phe,
      or Pro
<221> NAME/KEY: MISC_FEATURE
<222> LOCATION: (4)..(4)
<223> OTHER INFORMATION: X4 is Cys or another amino acid capable of
      forming a covalent cross-link to X12
<221> NAME/KEY: MISC_FEATURE
<222> LOCATION: (5)..(5)
<223> OTHER INFORMATION: X5 is Pro, Asn, Gln, Ser, or Thr
<221> NAME/KEY: MISC_FEATURE
<222> LOCATION: (6)..(6)
<223> OTHER INFORMATION: X6 is Ala, Asn, Asp, Gln, Glu, Gly, Ile, Leu,
      Met, Phe, Pro, Ser,Thr, Trp, Tyr, or Val
<221> NAME/KEY: MISC_FEATURE
<222> LOCATION: (7)..(7)
<223> OTHER INFORMATION: X7 is Glu or Ser
<221> NAME/KEY: MISC_FEATURE
<222> LOCATION: (8)..(8)
<223> OTHER INFORMATION: X8 is Pro, Asp, Glu, Asn, Gln, Ser, Thr, or Tyr
<221> NAME/KEY: MISC_FEATURE
<222> LOCATION: (10)..(10)
<223> OTHER INFORMATION: X10 is Leu, Ile, Met, Asn, Gln, Ser, Thr, or Val
<221> NAME/KEY: MISC_FEATURE
<222> LOCATION: (11)..(11)
<223> OTHER INFORMATION: X11 is Phe, Trp, or Tyr
<221> NAME/KEY: MISC_FEATURE
<222> LOCATION: (12)..(12)
<223> OTHER INFORMATION: X12 is Cys or another amino acid capable of
      forming a covalent cross-link to X4
<221> NAME/KEY: MISC_FEATURE
<222> LOCATION: (13)..(13)
<223> OTHER INFORMATION: X13 is Phe, Trp, or Tyr
<221> NAME/KEY: MISC_FEATURE
<222> LOCATION: (14)..(14)
<223> OTHER INFORMATION: X14 is Pro, Ala, Gly, Asn, Gln, Ser, Thr, Tyr,
      Asp, Glu, or His
<221> NAME/KEY: MISC_FEATURE
<222> LOCATION: (15)..(15)
<223> OTHER INFORMATION: X15 is Ala, Ile, Leu, Met, Phe, Pro, Trp, Val,
      Asn, Gln, Gly, Ser, Thr, Tyr, or His

<400> SEQUENCE: 41

Trp Xaa Xaa Xaa Xaa Xaa Xaa Xaa Trp Xaa Xaa Xaa Xaa Xaa Xaa
1               5                   10                  15

<210> SEQ ID NO 42
<211> LENGTH: 9
<212> TYPE: PRT
<213> ORGANISM: Artificial Sequence
<220> FEATURE:
<223> OTHER INFORMATION: fibrin binding polypeptides
<221> NAME/KEY: MISC_FEATURE
<222> LOCATION: (2)..(2)
<223> OTHER INFORMATION: X2 is Pro, Asn, Gln, Ser, or Thr
<221> NAME/KEY: MISC_FEATURE
<222> LOCATION: (3)..(3)
<223> OTHER INFORMATION: X3 is Ala, Asn, Asp, Gln, Glu, Gly, Ile, Leu,
      Met, Phe, Pro, Ser,Thr, Trp, Tyr, or Val
<221> NAME/KEY: MISC_FEATURE
<222> LOCATION: (4)..(4)
<223> OTHER INFORMATION: X4 is Glu or Ser
<221> NAME/KEY: MISC_FEATURE
<222> LOCATION: (5)..(5)
<223> OTHER INFORMATION: X5 is Pro, Asp, Glu, Asn, Gln, Ser, Thr, or Tyr
<221> NAME/KEY: MISC_FEATURE
<222> LOCATION: (7)..(7)
<223> OTHER INFORMATION: X7 is Leu, Ile, Met, Asn, Gln, Ser, Thr, or Val
<221> NAME/KEY: MISC_FEATURE
<222> LOCATION: (8)..(8)
<223> OTHER INFORMATION: X8 is Phe, Trp, or Tyr

<400> SEQUENCE: 42

Cys Xaa Xaa Xaa Xaa Trp Xaa Xaa Cys
1               5
```

<210> SEQ ID NO 43
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 43

Cys Tyr Gly Glu Ser Gly Ile Phe Cys
1               5

<210> SEQ ID NO 44
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 44

Cys Thr Gly Glu Pro Gly Pro Ile Cys
1               5

<210> SEQ ID NO 45
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 45

Cys Gln Leu Gly Tyr Arg Thr Tyr Cys
1               5

<210> SEQ ID NO 46
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 46

Cys Asp Gly Glu Pro Trp Leu Phe Cys
1               5

<210> SEQ ID NO 47
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 47

Cys Gly Trp Gly Ser Trp Lys Phe Cys
1               5

<210> SEQ ID NO 48
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 48

Cys Gly Trp Gly Ser Gly Lys Leu Cys
1               5

```
<210> SEQ ID NO 49
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 49

Cys Pro Gly Glu Pro Trp Thr Phe Cys
1               5

<210> SEQ ID NO 50
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 50

Cys Pro Gly Glu Pro Trp Thr Phe Cys
1               5

<210> SEQ ID NO 51
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 51

Cys Pro Gly Tyr Leu Arg Ser Leu Cys
1               5

<210> SEQ ID NO 52
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 52

Cys Pro Gly Glu Pro Trp Ser Phe Cys
1               5

<210> SEQ ID NO 53
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 53

Cys Arg Gly Glu Ser Trp Pro Tyr Cys
1               5

<210> SEQ ID NO 54
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 54

Cys Pro Gly Tyr Lys Arg Gln Phe Cys
1               5
```

-continued

```
<210> SEQ ID NO 55
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 55

Cys Gly Gln Glu Ser Arg Thr Phe Cys
1               5

<210> SEQ ID NO 56
<211> LENGTH: 9
<212> TYPE: PRT
<213> ORGANISM: Artificial Sequence
<220> FEATURE:
<223> OTHER INFORMATION: fibrin binding polypeptides

<400> SEQUENCE: 56

Cys Phe Gln Lys Gly Gly Thr Leu Cys
1               5
```